(12) United States Patent
Kanemoto et al.

(10) Patent No.: US 9,234,861 B2
(45) Date of Patent: Jan. 12, 2016

(54) ELECTRODE FOR ELECTROCHEMICAL MEASUREMENT, ELECTROLYSIS CELL FOR ELECTROCHEMICAL MEASUREMENT, ANALYZER FOR ELECTROCHEMICAL MEASUREMENT, AND METHODS FOR PRODUCING SAME

(75) Inventors: Hiroshi Kanemoto, Hitachinaka (JP); Haruo Akahoshi, Hitachi (JP); So Oguchi, Mito (JP); Kenta Imai, Hitachinaka (JP); Taku Sakazume, Hitachinaka (JP); Hiroshi Yoshida, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 164 days.

(21) Appl. No.: 13/992,514

(22) PCT Filed: Dec. 6, 2011

(86) PCT No.: PCT/JP2011/078137
§ 371 (c)(1),
(2), (4) Date: Jun. 7, 2013

(87) PCT Pub. No.: WO2012/077660
PCT Pub. Date: Jun. 14, 2012

(65) Prior Publication Data
US 2013/0248378 A1 Sep. 26, 2013

(30) Foreign Application Priority Data
Dec. 7, 2010 (JP) .................................. 2010-272128
Jan. 28, 2011 (JP) .................................. 2011-016434

(51) Int. Cl.
*G01N 27/30* (2006.01)
*C25B 11/04* (2006.01)
(Continued)

(52) U.S. Cl.
CPC ............ *G01N 27/30* (2013.01); *C25B 11/0426* (2013.01); *C25B 11/0431* (2013.01);
(Continued)

(58) Field of Classification Search
CPC ............ C25B 11/0426; C25B 11/0431; C25B 11/0484; H01M 4/92; H01M 4/921; H01M 4/923
See application file for complete search history.

(56) References Cited

U.S. PATENT DOCUMENTS 4,496,454 A  1/1985  Berger
4,995,550 A  2/1991  Appl et al.
(Continued)

FOREIGN PATENT DOCUMENTS

CN   101348872 A   1/2009
EP   0859228 A2   8/1998
(Continued)

OTHER PUBLICATIONS

Buichi Ise, Shinsaku Meguro, and Osamu Takagi, "Photoelectrochemical Behavior of TiO2-Pt Composite Electrodes by Dispersion Plating", Tohoku Institute of Technology Bulletin 1 Science and Engineering, Japan, Mar. 1987, No. 7, pp. 31-38.
(Continued)

*Primary Examiner* — Nicholas A Smith
(74) *Attorney, Agent, or Firm* — Volpe and Koenig, P.C.

(57) ABSTRACT

Provided are an electrode, an electrolysis cell, and an electrochemical analyzer that improve the long-term stability of analysis data. A working electrode, a counter electrode, and reference electrode are disposed in an electrolysis cell. The working electrode is obtained by forming a lead wire in a composite material having platinum or a platinum alloy as a base material, in which a metal oxide is dispersed, or in a laminated material obtained by laminating a valve metal and platinum such that the cross sectional crystal texture in the thickness direction of the platinum is formed in layers and the thickness of each layer of the platinum is 5 micrometers or less. The metal oxide is selected from among zirconium oxide, tantalum oxide, and niobium oxide, and the metal oxide content of the platinum or the platinum alloy is 0.005 to 1 wt % in terms of the zirconium, tantalum, or niobium metal.

6 Claims, 17 Drawing Sheets

(51) Int. Cl.
  *H01M 4/92* (2006.01)
  *G01N 27/327* (2006.01)
  *G01N 33/49* (2006.01)

(52) U.S. Cl.
  CPC ........ *C25B11/0484* (2013.01); *G01N 27/3271* (2013.01); *G01N 33/4915* (2013.01); *H01M 4/92* (2013.01); *H01M 4/921* (2013.01); *H01M 4/923* (2013.01)

(56) References Cited

U.S. PATENT DOCUMENTS

| | | | | |
|---|---|---|---|---|
| 5,009,766 | A | * | 4/1991 | Lauks .................. 204/403.14 |
| 5,372,838 | A | | 12/1994 | Aoki et al. |
| 6,451,225 | B1 | * | 9/2002 | Leland et al. .............. 252/700 |
| 7,378,005 | B2 | * | 5/2008 | Kaneda et al. ........ 204/290.13 |
| 2010/0178583 | A1 | * | 7/2010 | Han et al. .................. 429/483 |

FOREIGN PATENT DOCUMENTS

| | | | | |
|---|---|---|---|---|
| JP | 02-066188 | A | | 3/1990 |
| JP | 02-200790 | A | | 8/1990 |
| JP | 05-180796 | A | | 7/1993 |
| JP | 06-222037 | A | | 8/1994 |
| JP | 10-288592 | A | | 10/1998 |
| JP | 2001-262388 | A | | 9/2001 |
| JP | WO 2009091025 A1 | * | 7/2009 | .......... H01M 4/8605 |
| JP | 2010-095764 | A | | 4/2010 |

OTHER PUBLICATIONS

Buichi Ise, Shinsaku Meguro and Osamu Takagi, "Photoelectrochemical Behavior of TiO2-Pt Composite Electrodes by Dispersion Plating", Memoirs of the Tohoku Institute of Technology, Ser. I, Science and Engineering, No. 7, Mar. 1987, pp. 31-38.
Chinese Office Action, Chinese Patent Appln. No. 201180058358.4, Feb. 17, 2015, 7 pgs.

* cited by examiner

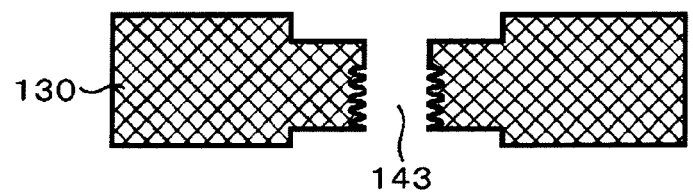
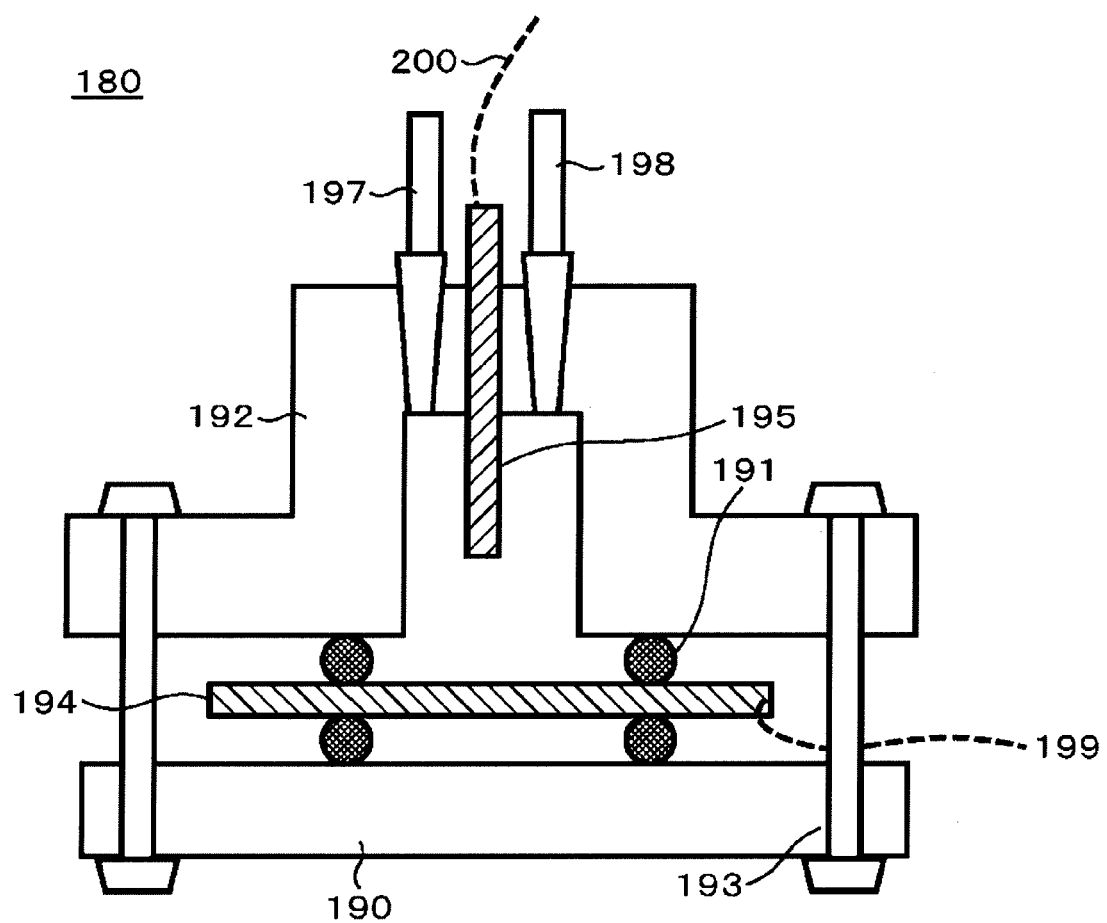

FIG.17

| | BASE | ADDED METAL OXIDE | METAL OXIDE CONTENT (%) | PREFERENTIAL ORIENTATION RATIO (%) [*1] | ANALYTE | VARIATION RANGE (%) [*2] |
|---|---|---|---|---|---|---|
| EMBODIMENT 1 | Pt | ZIRCONIUM OXIDE | 0.2 | 95 | THYROID STIMULATING HORMONE | 4.2 |
| EMBODIMENT 2 | Pt | ZIRCONIUM OXIDE | 0.2 | 96 | THYROID STIMULATING HORMONE | 3.8 |
| EMBODIMENT 3 | Pt | ZIRCONIUM OXIDE | 0.1 | 85 | | 5.0 |
| EMBODIMENT 4 | Pt | NIOBIUM OXIDE | 0.06 | 87 | GLUCOSE | 4.0 |
| EMBODIMENT 5 | Pt | TANTALUM OXIDE | 0.08 | 90 | UREA | 2.5 |
| EMBODIMENT 6 | PtAu | ZIRCONIUM OXIDE | 0.1 | 85 | CHOLESTEROL | 5.0 |
| EMBODIMENT 7 | PtRh | ZIRCONIUM OXIDE | 0.15 | 90 | URIC ACID | 5.3 |
| EMBODIMENT 8 | Pt | ZIRCONIUM OXIDE | 0.9 | 86 | CREATININE | 7.7 |
| EMBODIMENT 9 | Pt | ZIRCONIUM OXIDE | 0.004 | 82 | CREATININE | 12.3 |
| EMBODIMENT 10 | Pt | ZIRCONIUM OXIDE | 0.2 | 89 | FATTY ACID | 5.1 |
| EMBODIMENT 11 | Pt | ZIRCONIUM OXIDE | 0.2 | 83 | BILIRUBIN | 5.3 |
| EMBODIMENT 12 | Pt | ZIRCONIUM OXIDE | 9.7 | 47 | THYROID STIMULATING HORMONE | 8.7 |
| EMBODIMENT 13 | Pt | NIOBIUM OXIDE | 5.9 | 46 | THYROID STIMULATING HORMONE | 9.4 |
| EMBODIMENT 14 | Pt | TANTALUM OXIDE | 8.1 | 44 | THYROID STIMULATING HORMONE | 9.2 |
| COMPARATIVE EXAMPLE 1 | Pt | — | — | 54 | THYROID STIMULATING HORMONE | 10.3 |
| COMPARATIVE EXAMPLE 2 | | | | 63 | GLUCOSE | 4.2 |
| COMPARATIVE EXAMPLE 3 | | | | 38 | UREA | 3.7 |
| COMPARATIVE EXAMPLE 4 | | | | 55 | CHOLESTEROL | 7.3 |
| COMPARATIVE EXAMPLE 5 | | | | 48 | URIC ACID | 8.8 |
| COMPARATIVE EXAMPLE 6 | | | | 41 | CREATININE | 11.2 |
| COMPARATIVE EXAMPLE 7 | | | | 55 | CREATININE | 12.6 |
| COMPARATIVE EXAMPLE 8 | | | | 49 | FATTY ACID | 7.2 |
| COMPARATIVE EXAMPLE 9 | | | | 77 | BILIRUBIN | 6.6 |

*1) BASED ON X-RAY DIFFRACTION ANALYSIS RESULT OF ELECTRODE SURFACE.
*2) DIFFERENCE BETWEEN THE 60,000TH AND THE 1ST ANALYSIS VALUES.

ELECTRODE SURFACE

| | STRUCTURE OF CRYSTAL TEXTURE IN PLATINUM PART CROSS-SECTION [*1] | PREFERENTIAL ORIENTATION RATIO OF PLATINUM PART (%) [*2] | ANALYTE | VARIATION RANGE (%) [*3] |
|---|---|---|---|---|
| EMBODIMENT 15 | LAYER-LIKE (FINE CRYSTAL TEXTURE WITH EACH CRYSTAL LAYER THICKNESS OF 5μm OR LESS) | 97 | THYROID STIMULATING HORMONE | 4.4 |
| EMBODIMENT 16 | | 98 | THYROID STIMULATING HORMONE | 4.2 |
| EMBODIMENT 17 | | 92 | | 5.1 |
| EMBODIMENT 18 | | 85 | GLUCOSE | 4.1 |
| EMBODIMENT 19 | | 92 | UREA | 2.8 |
| EMBODIMENT 20 | | 88 | CHOLESTEROL | 5.8 |
| EMBODIMENT 21 | | 90 | URIC ACID | 6.5 |
| EMBODIMENT 22 | | 83 | CREATININE | 7.9 |
| EMBODIMENT 23 | | 91 | CREATININE | 9.8 |
| EMBODIMENT 24 | | 81 | FATTY ACID | 5.9 |
| EMBODIMENT 25 | | 92 | BILIRUBIN | 4.3 |
| COMPARATIVE EXAMPLE 10 | COARSE CRYSTAL | 54 | THYROID STIMULATING HORMONE | 10.3 |
| COMPARATIVE EXAMPLE 11 | | 63 | GLUCOSE | 4.2 |
| COMPARATIVE EXAMPLE 12 | | 38 | UREA | 3.7 |
| COMPARATIVE EXAMPLE 13 | | 55 | CHOLESTEROL | 7.3 |
| COMPARATIVE EXAMPLE 14 | | 48 | URIC ACID | 8.8 |
| COMPARATIVE EXAMPLE 15 | | 41 | CREATININE | 11.2 |
| COMPARATIVE EXAMPLE 16 | | 55 | CREATININE | 12.6 |
| COMPARATIVE EXAMPLE 17 | | 49 | FATTY ACID | 7.2 |
| COMPARATIVE EXAMPLE 18 | | 77 | BILIRUBIN | 6.6 |

*1) BASED ON EBSP ANALYSIS RESULT.   *2) BASED ON XRD ANALYSIS RESULT.
*3) DIFFERENCE BETWEEN THE 60,000TH AND 1ST ANALYSIS VALUES.

ELECTRODE FOR ELECTROCHEMICAL MEASUREMENT, ELECTROLYSIS CELL FOR ELECTROCHEMICAL MEASUREMENT, ANALYZER FOR ELECTROCHEMICAL MEASUREMENT, AND METHODS FOR PRODUCING SAME

TECHNICAL FIELD

The present invention relates to electrodes for electrochemical measurement, electrolysis cells for electrochemical measurement, an electrochemical analysis apparatus, and manufacturing methods thereof; more particularly, it relates to an electrode for electrochemical measurement, an electrolysis cell for electrochemical measurement, and an analyzer for electrochemical analysis with which minute amounts of chemical components contained in liquid samples such as blood and urine are analyzed electrochemically.

BACKGROUND ART

Electrochemical measurement is capable of performing high-sensitivity measurement with use of relatively simple apparatus configurations and is frequently used in the field of analytical chemistry. Available electrochemical measurement schemes include potentiometry, amperometry, voltammetry, and impedance measurement, and further include other detection methods such as methods for detecting photons by combinatorial use of these with an optical element or the like, for example.

Generally, an electrode used for electrochemical measurement is frequently made of a platinum group metal—especially, platinum—in the light of its excellent chemical stability characteristics. In recent years, also in the analysis of chemical components contained in liquid samples such as blood and urine, platinum is used as the electrode to be built in a flow cell.

For example, Patent Literature 1 discloses that in the case of continuous measurement of a chemical component in blood or urine repetitive measurement is enabled through a process of applying a plurality of electrical potentials between a working electrode and a counter electrode on a per-analysis basis, in addition to cleaning and main measurement.

An example using a mixture material of platinum and metal oxide as the electrode is found in Patent Literature 2, which discloses therein an electrode comprising a surface layer formed on the surface of a metallic base substance by solid solution of tin oxide and antimony oxide and a mixture layer of a platinum-group metal or its oxide and an oxide of IV- or V-group metal as an intermediate layer between the metal base substance and the surface layer. Additionally, Patent Literature 3 discloses an electrode for electrolysis having an outer layer above a surface of a titanium or a titanium alloy body with an intermediate layer being laid therebetween, wherein the outer layer is made of a mixed metal oxide comprising iridium oxide, platinum, and at least one kind of metal oxide selected from the group consisting of niobium oxide, tantalum oxide, and zirconium oxide.

Patent Literature 4 discloses therein an oxygen sensor's electrode comprising either an oxide semiconductor or a solid electrolyte, the surface of which is coated with an electrode material containing an oxide of aforementioned the aforementioned constituent metal and platinum.

Concerning the electrode material containing a platinum-group metal, Patent Literature 5 describes therein use of a platinum-group metal for the counter electrode and the working electrode. Additionally, Patent Literature 6 discloses an electrode for electrochemical reaction which is composed with a valve metal such as titanium, tantalum, or zirconium and platinum by thermal pressing, and also discloses a manufacturing method of the electrode.

Furthermore, Patent Literature 7 discloses an electrode with sequential formation of a platinum alloy coat layer and a coat layer made of iridium oxide and/or platinum oxide on a titanium, niobium, or tantalum base material, as an electrode for electrolyzing a salt solution to produce strongly acidic water having bactericidal action and an insoluble electrode used for certain applications such as electrolytic cleaning treatment of waste water containing organic substances.

CITATION LIST

Patent Literature

Patent Literature 1: JP-A-06-222037
Patent Literature 2: JP-A-2010-095764
Patent Literature 3: JP-A-02-200790
Patent Literature 4: JP-A-05-180796
Patent Literature 5: JP-A-10-288592
Patent Literature 6: JP-A-02-066188
Patent Literature 7: JP-A-2001-262388

SUMMARY OF INVENTION

Technical Problem

In cases where a platinum-group metal, especially platinum, is used as an electrode, it shows very excellent characteristics in analyses to be experimentally performed for a few dozen times to several hundred times.

However, in the analysis system shown in Patent Literature 1, for example, in the analysis of chemical components contained in a liquid sample such as blood or urine, the electrode surface is gradually corroded in a case where a sample that contains large amounts of protein and halogen elements in its components is subjected to iterative measurement for a long time period or, alternatively, in case a sample containing a strong alkaline component such as potassium hydroxide as a cleaning agent for cleaning an electrode surface is brought into contact with the electrode surface and then a voltage is repeatedly applied thereto for a prolonged period. As a result, the electrode's surface condition varies, posing a problem that it exerts a bad influence on measurement results.

In Patent Literature 2, a mixture material of platinum and metal oxide is used as the intermediate layer in order to improve adhesiveness and electrical conductivity between a metal base substance and a solid solution of tin oxide and antimony oxide actually causing electrochemical reaction. In Literature 2, the mixture material of platinum and metal oxide is not used as the surface for causing electrochemical reaction. Although the solid solution of tin oxide and antimony oxide becomes the surface actually causing electrochemical reaction, with samples containing strong alkaline component as intended by the present inventors dissolution from the electrode surface is large, thereby causing the surface state to vary significantly and resulting in a failure in improving the stability of analytical data.

Although in Patent Literature 3 the outer layer's mixed metal oxide is an electrode material formed by sintering and it is known that aforementioned material exerts effect as an anode for seawater electrolysis, metal surface treatment, metal foil fabrication/recovery, and the like, wastage of the electrode is severe with an increase in variation of electrode surface state, resulting in lessened effect on improvement of the stability of analysis data in the inventors' intended case of iteratively performing measurement of a sample containing large amounts of protein and halogen element in its components for an extended period of time or, alternatively, in the case of iteratively applying a voltage over time while contacting a sample with the electrode surface, where sample contains a strong alkaline component such as potassium hydroxide, as the cleaning agent for cleaning the electrode surface. In addition, due to the presence of cracks in the electrode surface of the aforementioned material, it was seen in some cases that residue of the liquid sample adversely affects a measurement result of the next sample.

In Patent Literature 4, in the case of letting stabilized zirconia be a solid electrolyte for a detection electrode of an oxygen sensor for example, its surface is coated with a mixture of platinum and zirconium oxide, thereby improving adhesion with the underlying solid electrolyte and also achieving improvement of reaction efficiency owing to the formation of a three-phase interface. Although details are not disclosed therein, it is considered that the platinum/zirconium mixture is low in film density in view of the fact that an advantage of reaction efficiency improvement was obtained. More specifically, it is conceivable that the aforementioned mixture as the electrode for iterative measurement of chemical components contained in a liquid sample as intended by the inventors can result in a decrease in reliability of measurement result due to residue of the liquid sample in a film.

As is commonly known, platinum is a high-priced metal and, as shown in Patent Literatures 5 and 6, it is well known to employ composite electrodes made of compounds of a platinum-group metal, platinum, a titanium metal, and the like.

However, in the above-stated composite electrodes, there are no examples arranged to control the crystalline texture and orientation property of a platinum layer.

The inventors of the present application have conducted diligent studies to reveal that analysis data are affected by the surface state of the electrode—particularly, the crystalline texture and crystal orientation property—in the analysis that uses the same electrode to measure a plurality of times a very small concentration of chemical component contained in a liquid sample such as blood or urine.

It is an objective of the present invention to realize an electrode capable of performing proper analytical measurement while letting data remain stable over a lengthy period, an electrolysis cell using this electrode, and an electrochemical analysis apparatus using the same.

Furthermore, it is another object of the present invention to realize an electrode for the electrochemical measurement use which reduces the amount of platinum and has enough mechanical strength but is less in variability of electrode surface state, an electrode capable of performing adequate analytical measurement with long-term data stability by using the aforementioned electrode, and an electrolysis cell and an electrochemical analysis apparatus using such the electrode.

Solution to Problem

To attain the foregoing objects, the present invention is arranged as follows.

An electrode of the present invention is an electrode for electrochemical measurement used in an electrochemical analysis apparatus which measures electrochemical response of a chemical component contained in a liquid sample and is an electrode which is made by forming a lead wire to a composite material in which a metal oxide is contained as being dispersed in a base material that is made of platinum or a platinum alloy. As the metal oxide zirconium oxide, tantalum oxide, niobium oxide, or the like is preferable and the content ratio in the platinum or the platinum alloy is set at 0.005 to 1% in the metal-equivalent value. It is noted that the percentage of the content ratio of a chemical component in this description is designated in weight percent (wt %).

The electrode of the present invention is an electrode in which the orientation ratio of one of a plurality of crystal directions obtained is 80% or greater when letting the orientation ratio (%) of a crystal direction obtained by X-ray diffraction measurement of a surface of the electrode be $I(hkl)/\Sigma I(hkl) \times 100$ (where $I(hkl)$ is a diffraction intensity integration value of each plane, and $\Sigma I(hkl)$ is the total sum of diffraction intensity integration values of $(hkl)$).

The electrode of the present invention is an electrode in which a material of an electrode is embedded in an insulative resin except for a part of the surface of the electrode.

An electrolysis cell of the present invention is an electrolysis cell for measuring electrochemical response of a chemical component contained in a liquid sample and is an electrolysis cell which has the above-stated electrodes of this invention as a counter electrode, a reference electrode, and a working electrode disposed inside the cell. It may alternatively be a flow cell to which an injection port for injecting into the cell and an exhaust port for discharging to exterior of the cell a liquid sample are disposed.

An electrochemical analysis apparatus of the present invention is an electrochemical analyzer which includes the above-stated electrolysis cell of this invention; a solution injection means which injects into the electrolysis cell a solution to be measured, a buffer solution, and a cleaning solution; a potential application means which applies potentials to the working electrode, the counter electrode, and the reference electrode; and a measuring means which is connected to the working electrode, the counter electrode, and the reference electrode, and measures electrochemical characteristics of the solution to be measured.

A method for producing an electrode for electrochemical measurement of the present invention is a method following the steps (a) to (d) below.

The steps comprise (a) electroding by providing a lead wire to a composite material in which a metal oxide is contained as being dispersed in a base material, which is made of platinum or a platinum alloy (b) embedding the electrode in an insulative resin except for one part of a surface of the electrode, (c) performing mechanical polishing on a surface of the electrode embedded in the resin, and (d) performing electrolytic polishing on the surface of the electrode to remove a surface alteration layer. It is preferable that the electrolytic polishing is a step of iteratively applying for a plurality of times a potential between potentials of from a hydrogen producing region to an oxygen producing region in an electrolytic solution. It is preferable that a waveform of the applied potential is a rectangular wave. It is further preferable that, after the electrolytic polishing processing, cyclic voltammetry is carried out so that a state of a surface of an electrode is diagnosed from the area ratio of at least two of a plurality of hydrogen absorption/desorption peaks seen in the measurement result and electrolytic polishing is repeated until a prescribed peak ratio is reached.

A method for producing the electrolysis cell of the present invention is a method following the steps (a) to (e) below.

The steps comprise (a) electroding by providing a lead wire to a composite material in which a metal oxide is contained as being dispersed in the base material, which is made of platinum or a platinum alloy, (b) embedding the electrode by an adhesive agent into an insulative substrate having a solution injection port and an exhaust port formed in advance, (c) performing mechanical polishing on a surface of the electrode embedded in the insulative substrate, (d) performing electrolytic polishing on the surface of the electrode to remove a surface alteration layer, and (e) integrating by lamination the insulative substrate with the electrode on which polishing was performed being embedded therein, a sealing member having an opening, and another insulative substrate, and adding thereto a counter electrode and a reference electrode.

An apparatus for producing an electrode for electrochemical measurement of the present invention is a manufacturing apparatus which comprises (a) an electroding unit which provides a lead wire to a composite material in which a metal oxide is contained in as being dispersed in the base material, which is made of platinum or a platinum allow, (b) a resin embedding unit which embeds the electrode in an insulative resin except for one part of a surface of the electrode, (c) a mechanical polishing unit which performs mechanical polishing on a surface of the electrode embedded in the resin, and (d) an electrolytic polishing unit which performs electrolytic polishing on the surface of the electrode surface to remove a surface alteration layer.

An apparatus for producing an electrolysis cell of the present invention is a manufacturing apparatus which comprises (a) an electroding unit which provides a lead wire to a composite material in which a metal oxide is contained as being dispersed in the base material, which is made of platinum or a platinum allow, (b) a resin embedding unit which embeds the electrode by an adhesive agent into an insulative substrate having a solution injection port and an exhaust port formed in advance, (c) a mechanical polishing unit which performs mechanical polishing on a surface of an electrode embedded in the insulative substrate, (d) an electrolytic polishing unit which performs electrolytic polishing on the surface of the electrode to remove a surface alteration layer, and (e) a cell assembling unit which integrates by lamination the insulative substrate with the electrode on which polishing was performed being embedded therein, a sealing member having an opening, and another insulative substrate, and adds thereto a counter electrode and a reference electrode.

The electrode for electrochemical measurement of the present invention is arranged so that a valve metal of any of Ti, Ta, Nb, Zr, Hf, V, Mo, and W and platinum are laminated with each other and a cross-sectional crystal texture of the platinum part in the plate thickness direction is formed in a layer-like form with respect to the surface of the electrode.

Also, an electrochemical analysis apparatus of the present invention comprises an electrolysis cell having a working electrode, a counter electrode, and a reference electrode disposed therein; a solution injection mechanism which injects a solution under measurement and a buffer solution in the electrolysis cell; a potential application means which applies potentials to the working electrode, the counter electrode, and the reference electrode; and a measuring means which is connected to the working electrode, the counter electrode, and the reference electrode and measures electrochemical characteristics of the solution under measurement, in which the working electrode has a valve metal of any of Ti, Ta, Nb, Zr, Hf, V, Mo, and W and platinum being laminated with each other, and a cross-sectional crystal texture of the platinum part in the plate thickness direction being formed in a layer-like form with respect to the surface of the electrode.

Furthermore, a method for producing an electrode for electrochemical measurement to be used in an electrochemical analysis apparatus of the present invention comprises the steps of forming a multilayer electrode as laminating a valve metal of any of Ti, Ta, Nb, Zr, Hf, V, Mo, and W and platinum into a plate-like form by cold rolling so that a cross-sectional crystal texture in plate thickness direction of the platinum in a layer-like form with respect to a surface of an electrode with a thickness of each layer of the platinum being equal to or less than 5 micrometers, performing mechanical polishing on the formed multilayer electrode, and electrochemically removing a surface alteration layer of the multilayer electrode.

Further, an apparatus for producing an electrode for electrochemical measurement to be used in an electrochemical analysis apparatus of the present invention comprises a platinum plate machining unit which produces a platinum plate with a prescribed plate thickness as pressing platinum in a nitrogen atmosphere and heating it to perform hot rolling, a platinum plate cold-rolling unit which cold rolls the platinum plate, a surface oxide film removing unit which places the platinum plate processed at the platinum plate cold-rolling unit and a titanium plate in a vacuum and dry etches a surface of the titanium plate so that a surface oxide layer is removed, a multilayer electrode forming unit which forms a multilayer electrode of platinum and titanium as laminating the platinum plate and the titanium plate and performing cold rolling in a vacuum atmosphere in such a manner that a film thickness of the platinum plate becomes a prescribed thickness so that a cross-sectional crystal texture in a plate thickness direction of the platinum in a layer-like form with respect to a surface of the electrode with a thickness of each layer of the platinum is equal to or less than 5 micrometers, a cutting unit which cuts the formed multilayer electrode into a prescribed size, an electroding unit which connects electrically a platinum surface of the cut multilayer electrode and a conductive wire together, a resin embedding unit which embeds in an insulative resin using an adhesive agent in such a manner that only a platinum surface of the multilayer electrode connected with the conductive wire is exposed with a prescribed area, a mechanical polishing unit which performs mechanical polishing on the platinum surface of the embedded multilayer electrode, and an electrolytic polishing unit which repeats scanning of electrical potential to the mechanically polished multilayer electrode in an electrolytic solution at a prescribed potential and a prescribed potential scanning rate.

Advantageous Effects of Invention

According to the present invention, by using an electrode which is made by forming a lead wire to a composite material in which a metal oxide is contained as being dispersed in a base material that is made of platinum or a platinum alloy, preferably, the electrode in which the metal oxide is zirconium oxide, tantalum oxide, or niobium oxide and its content ratio in the platinum or the platinum alloy is set at 0.005 to 1% in the metal-equivalent value, particularly, the electrode in which the orientation ratio of one of a plurality of crystal directions obtained by X-ray diffraction measurement of a surface of the electrode surface is 80% or greater, and the electrolysis cell and the electrochemical analysis apparatus using such the electrode, it becomes possible to secure the state of the surface of the electrode which is stable in a long term and obtain measurement results with high reliability in the electrochemical analysis for measuring electrochemical response of a chemical component contained in a liquid sample, in particular, in the analysis that performs iterative measurement of a chemical component contained in a liquid sample such as blood or urine.

Furthermore, according to the present invention, it is possible to realize an electrode for electrochemical measurement which reduces the amount of platinum and has enough mechanical strength but is less in variation of electrode surface state, an electrochemical analysis apparatus using this electrode and capable of performing proper analytical measurement with long-term data stability, a manufacturing method of the electrode for electrochemical measurement, and a manufacturing apparatus of the electrode for electrochemical measurement.

Other objects, features, and advantages of the invention will become apparent from the following description of the embodiments of the invention taken in conjunction with the accompanying drawings.

BRIEF DESCRIPTION OF DRAWINGS

FIG. 14C is a cross-sectional view of an insulative substrate in another further example of the flow cell used for an electrochemical analysis apparatus of an embodiment of the present invention;

FIG. 15 is a cross-sectional assembly diagram of still another further example of the flow cell used for an electrochemical analysis apparatus of an embodiment of the present invention;

FIG. 17 is a table showing content rates of added metal oxide, preferential orientations of platinum or platinum alloy as a base material, analytes, and variation ranges of Embodiments 1 to 14 of the present invention and Comparative Examples 1 to 9;

FIG. 24 is a table showing preferential orientations of platinum part, analytes, and variation ranges of Embodiments 15 to 25 of the present invention and Comparative Examples 10 to 18.

DESCRIPTION OF EMBODIMENTS

Figure 1:
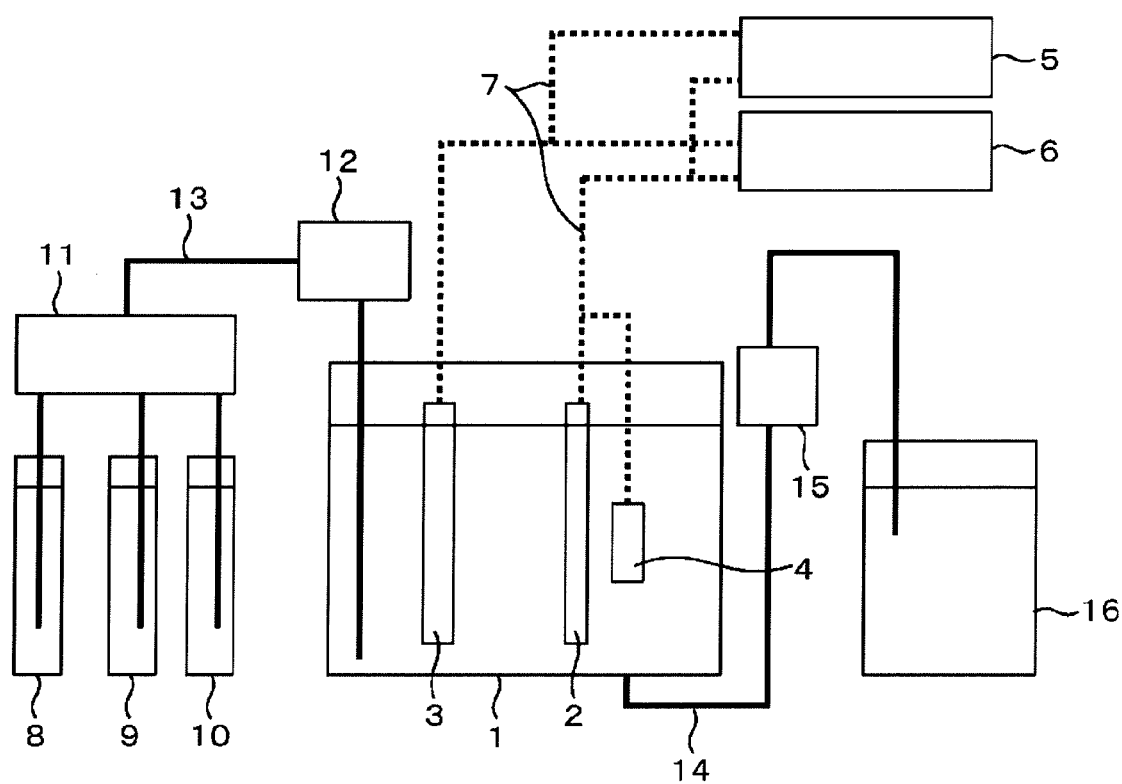
FIG. 1 is an overall configuration diagram of an electrochemical analysis apparatus in accordance with one embodiment of the present invention.

Embodiments of the present invention will be explained with reference to the accompanying drawings below.

Prior to explanation of embodiments of the present invention, an explanation will be given on principal concepts of the present invention.

The inventors performed analysis, in various ways, about the cause for variation of measurement results in cases where measurement is repeatedly carried out over an extended time period in the analysis of chemical components contained in a liquid sample such as blood or urine. As a result, it was revealed that it arises mainly from changes in electrode surface state due to iteration of analysis.

Namely, when repeating over time the process of applying electrical potential in a liquid sample containing therein protein or the like and the process of applying electrical potential in a liquid containing a strong alkali component such as potassium hydroxide serving as a cleaning agent for cleaning an electrode surface, the electrode surface is gradually etched away, causing the state of a surface after iterative analyses to vary from that at the initial stage of analysis. This adversely affects a measurement result as result.

Upon inspection of the platinum surface's etching behavior, in the case of a platinum electrode with its crystalline texture coarsened due to thermal processing for example, a case was seen where with repeated execution of analysis, an easily etchable crystal face preferentially undergoes elution, causing local generation of a relatively large concave portion within the electrode surface. This arises from a change in etching rate depending on the surface's crystal direction. It was also revealed that in the case of a certain chemical component contained in the liquid sample, the reactivity differs depending on the crystal direction of electrode surface. Namely, it was ascertained that repeated analysis execution causes the ratio of each crystal direction exposed to the outermost surface to vary, resulting in the response amount of electrochemical reaction becoming different, thereby affecting analysis data. This phenomenon is such that in the case of placing the electrode in a flow cell, it is no longer possible to establish stable liquid flow, resulting in a failure to sufficiently perform the substitution of an analyte liquid and cleaning liquid, thereby disabling execution of adequate analysis.

Meanwhile, in cases where an electrode is used which is made finer in crystalline texture and has its crystal orientation property preferentially aligned to one direction, it was found out that even under the condition where the electrode surface is etched due to analysis iteration, the elution caused by etching progresses relatively uniformly in an electrode plane without forming local concave portions in the electrode plane, although it experiences generation of a number of fine holes formed by the etching, i.e., etch pits. Especially, in a system for selectively capturing a minute concentration of chemical component contained in a liquid sample such as blood or urine on the electrode using magnetic particles to analyze particles, it was found that the frictional force between etch pits created in the surface and magnetic particles increases, resulting in improvement of the stability of magnetic particles on the electrode, which in turn leads to stabilization of analysis data.

For the reason stated above, the conception was reached in which for improvement of the analysis data stability, it is effective that crystalline structure of an electrode material which actually causes electrochemical reaction is fine and that variation of the exposed crystal face under the condition that its surface is gradually etched away is suppressed.

One of electrode materials of the present invention is an oxide dispersion type composite material with a metal oxide being finely dispersed in a base material of either platinum or platinum alloy, as will be explained in greater detail below.

Concerning the platinum or the platinum alloy as the base material of the electrode of the present invention, platinum-rhodium, platinum-gold, platinum-iridium, or the like is selectable appropriately in accordance with the chemical component contained in a liquid sample. In the metal oxide dispersion type composite material as disclosed herein, the base material is either platinum or a platinum alloy in the bulk state And, when defining a void ratio to be a volume-equivalent percentage value of the ratio of voids existing in the base material to the base material, it is a material with its void ratio being less than or equal to 1%—preferably, 0.2% or less. Preferably, the hole diameters of the voids are 5 µm or less. When the void ratio goes above 1% and/or the hole diameters of voids exceed 5 µm, the voids existing in the base material are exposed to the top surface in the process of analysis iteration, thereby affecting analysis data in some cases.

The metal oxide in the metal oxide-dispersed composite material of the present invention stably exists in either the platinum or the platinum alloy that is the base material in a fabrication process of the composite material and serves, as one of its roles, to keep the base material's crystal texture fine. Desirably, the metal oxide existing in the electrode surface is the one that is small in contribution to electrochemical reaction within a wide pH range since it contacts with various kinds of electrolytic solutions such as a liquid sample. As can be seen from these reasons and a potential-pH diagram (Pourbaix diagram), oxides of zirconium, tantalum, niobium, or the like are usable.

Preferably, the content ratio of such metal oxide in the base material falls within a range of from 0.005 to 1%. In the case of being equal to or less than 0.005%, the amount of the oxide contained in base material is too low so that in some regions the base material's crystal becomes coarser in a location dependent manner. In the case of exceeding 1%, the contribution to electrochemical reaction becomes larger, thereby affecting analysis data and deteriorating the machinability. In the case of machining the electrode into a shape for which drawing-workability and malleability are required, it is preferable to set the dispersed particle concentration at 0.01 to 0.15% in order to enhance the machinability.

It is not always necessary for all the additive metal in the base material to be in the state of an oxide. For example, as a manufacturing method of the metal oxide dispersion type composite material there is the one that forms dispersed particles by oxidizing an added metal-holding platinum powder and then oxidizing added metals; however, in this case, all added metals are not strictly required to be converted to oxides in the oxidation processing—what is required is that a requisite quantity of dispersed particles are finely dispersed therein. To lessen the influence on the electrochemical reaction, it is preferable to sufficiently perform the oxidation treatment.

Although the shape of the composite material of the metal oxide dispersion type of the present invention is not specifically limited to a wire-like shape, a rod-like shape, a mesh-like shape, or the like, the one that has a plate-like shape formed by rolling treatment or the like is particularly good; preferably employable is the one that is enhanced in the crystal orientation property of composite material by execution of strong rolling during cold rolling.

The metal oxide-dispersed composite material is manufacturable by known methods.

An exemplary method is as follows. After having formed a platinum alloy with zirconium added to platinum, a platinum alloy powder is formed by the so-called flame spray coating method, which fuses and sprays the platinum alloy into water with a flame gun or the like, thereby forming a platinum alloy powder. This platinum alloy powder undergoes oxidation in an atmosphere of the air of high temperature. The oxidized platinum alloy powder is then subjected to compression molding to have a prescribed shape; thereafter, sintering is performed at high temperatures. The resultant molded body is applied shape-machining using an air hummer, cold rolling, and heating treatment for recrystallization.

Another method is as follows. Powder preparation-completed platinum is provided; then, chemical precipitation reaction is utilized to form zirconium hydroxide-supporting platinum which supports zirconium hydroxide. By using a powder of this zirconium hydroxide-supporting platinum, molding, sintering, forging, cold rolling, and heating for recrystallization are sequentially performed. To disperse the metal oxide uniformly in the finally completed product, it is preferable that the particle size of platinum powder of a starting material be set in a range of 0.05 to 10 μm.

Still another method is as follows. A platinum powder in the state that a zirconium oxide is supported in platinum is formed by coprecipitation method and this platinum powder is used to manufacture the composite material. Namely, a hexachloroplatinic acid solution and zirconium nitrate solution are mixed together; then, adding hydrazinehydrate as a reducing agent and calcium hydroxide as a pH regulator thereto causes coprecipitation reaction to take place, thus obtaining a platinum-zirconium hydroxide powder. Thereafter, percolation, desiccation, and sintering are performed to obtain the powder of zirconium oxide-holding platinum. Then, sintering, forging, cold rolling, and recrystallization are performed sequentially.

In the crystal orientation ratio of electrode surface, the metal oxide-dispersed composite material of the present invention is preferably arranged so that one of a plurality of crystal directions is oriented preferentially. The crystal orientation ratio of the electrode surface is defined by the following Equation (1).

$$\text{(Orientation Ratio of Crystal Direction)} = I(hkl)/\Sigma I(hkl) \times 100 \quad (1)$$

where I(hkl) is the diffraction intensity integration value of each face obtained by X-ray diffraction measurement of the electrode surface, and ΣI(hkl) is a total sum of diffraction intensity integration values of (hkl). Note here that in this description, the preferential orientation property is calculated from a diffraction intensity integration value of each of the (111) plane, the (200) plane, the (220) plane, and the (311) plane obtained by X-ray diffraction measurement, in accordance with Equation (1) presented above.

Although the preferable plane direction is not specifically limited, a metal oxide-dispersed composite material with any one of the (111), (200), (220), and (311) planes being preferentially oriented in the X-ray diffraction of the electrode surface is preferable. An electrode with a prescribed plane direction occupying 80% or more in peak integration value is preferable; more preferable is a material with the (220) plane's orientation ratio showing 80%. To that end, it is preferable to perform the cold rolling under the condition of the draft being set at 70% or greater—preferably, 90% or more—and further apply mechanical polishing and electrolytic polishing to the surface of resultant material as will be set forth later. Incidentally, the draft is defined by Equation (2) below.

$$\text{(Draft)} = (t_0 - t)/t_0 \times 100 \quad (2)$$

where in Equation (2) above, $t_0$ is the thickness before rolling, and t is the thickness after rolling.

The material of a lead wire connected to the metal oxide-dispersed composite material may be a widely used metallic material low in electrical resistance, such as copper, aluminum, silver, or platinum, or may be a wiring lead made of any one of such metals with its surface being dielectrically coated, although not specifically limited thereto. The connection between such the lead wire and the dispersion type composite material is achievable by known methods such as welding or soldering.

On occasions when defining the electrode area or when wanting to prevent either the lead wire material or a contact portion from being immersed in a liquid sample, it may be embedded in insulative resin except for part of the electrode surface. The insulative resin may be superior in chemical resistant such as fluorinated resin, polyethylene, polypropylene, polyester, polyvinyl chloride, epoxy resin, polyether-ether-ketone, polyimide, polyamide-imide, polystyrene, polysulfone, polyether sulfone, polyphenylene sulfide, and acrylic resin and also can be adequately chosen in accordance with a liquid sample as the analyte although it is not particularly limited to.

The electrode of the present invention may be fastened to an insulative substrate by using an adhesive agent. The insulative substrate may be made of a material similar to that of the above-stated insulative resin. A resin material with thermoplasticity, thermalsetting, or photohardening such as an epoxy-based or acrylic substance may be used as the adhesive agent; it is not specifically limited thereto and may be properly chosen as long as it is excellent in chemical resistance similar to the insulative resin.

In a case where the electrode is buried in an insulative resin or fixed to an insulative substrate, a clad material with another metal being disposed as an underlayer of the electrode of the present invention is usable. For example, a material in which the metal oxide-dispersed composite material and a valve metal such as titanium are adhered with each other may be used. As for the adhesion, it is needed to quickly adhere with platinum while exposing the metal surface of titanium because the surface of titanium or the like reacts with oxygen, carbon, nitrogen, and the like to form an inactive coating. To do this, for example, the inactive coating formed on the titanium surface is removed by etching or the like in a vacuum and, thereafter, it is forged while being contacted with the composite material, thereby enabling the adhesion. It is also possible to perform cold rolling after having the titanium and the metal oxide-dispersed composite material joined together by known explosive welding methods. It is more preferable to form it by contacting together the cold rolled metal oxide-dispersed composite material and the titanium having its surface platinum-plated and then applying forging thereto. In the case of applying the platinum plating to the titanium surface, surface may be treated with a sandblasting method or a chemical etching method as pretreatment for adhesiveness improvement. In the chemical etching method, there may be used a hydrofluoric acid, fluoride-containing hydrofluoric acid, concentrated sulfuric acid, hydrochloric acid, oxalic acid, or a mixed solution of them.

The plate thickness of underlayer metal is preferably 0.01 to 5 mm from a viewpoint of machinability of bending, cutting, or the like although not specifically limited thereto. The plate thickness of the metal oxide-dispersed composite material is preferably 0.01 to 0.3 mm. More preferably, it ranges from 0.02 to 0.15 mm. Under the influence of local heat and pressure concentration in the rolling process, a state of crystalline texture different from the inside may be formed in a top surface layer, the depth of which may reach about 0.01 mm from the surface layer according to circumstances. Due to this, it is preferable to set the thickness of metal oxide-dispersed composite material to 0.01 mm or greater and to use it while exposing the internal crystalline texture to the top surface after removal of the surface layer by mechanical polishing. When the thickness is 0.3 mm or more, the amount of platinum becomes greater, resulting in an increase in cost.

The metal oxide-dispersed composite material is preferably arranged so that its surface is mechanically polished as stated above. Moreover, it is preferable that electrolytic polishing is carried out after the mechanical polishing. Regarding the electrolytic polishing it is preferable to iteratively apply electrical potential between a hydrogen-producing region and an oxygen-producing region in an electrolytic solution that contains an acid or a strong alkali component such as potassium hydroxide. As for the waveform of the applied potential, a triangular waveform, a rectangular waveform, or the like may be used although there is no particular need to limit thereto in the present invention.

The aforementioned mechanical polishing and electrolytic polishing are particularly effective in the case of performing cold rolling treatment under the condition of a large draft. Namely, it was revealed that the crystal orientation property near the surface of a material formed through the rolling treatment inter alia is relatively random and local surface heating causes differences in crystal grain diameter and in orientation between the plate inside and its surface layer part. While a surface alteration layer formed by rolling is removed to some extent in the material after being mechanically polished, a surface alteration layer formed by pressurization during mechanical polishing and scars caused by abrasive particles still exist still. Also in the manufacturing method of the present invention, the cold rolling allows the inside of platinum to be in the state that it has crystal orientation property; however, it is conceivable that a surface alteration layer with irregular crystal orientation is formed. The mechanical polishing and electrolytic polishing are effective on removal of the aforementioned surface alteration layer, and can be said to be the process for exposing the material's internal part having high crystal orientation property.

As previously stated, according to investigation of the etching behavior of platinum surface, step-like differences take place in units of crystal direction-different textures due to a change in etching rate depending on the surface's crystal direction. Furthermore, when a crystal layer which can be seen by cross-section observation of the platinum in the plate thickness direction exceeds 5 µm, analysis iteration, that is, progression of etching, causes the electrode surface's unevenness to become prominent, resulting in variation of the electrode surface area.

Especially, in the case of a working electrode being placed in a flow cell, if such unevenness of the electrode surface is significant, a stable liquid flow can no longer be secured, leading to a failure to sufficiently perform the fluid replacement of an analyte liquid and a cleaning fluid, and resulting in the lack of an ability to perform proper analysis.

Consequently, it is also conceivable to lessen the crystal layer to thereby suppress large variation of the electrode surface area. Namely, in order to stabilize analysis data over a long time, it is effective to perform etching uniformly in the plate thickness direction while setting the thickness of platinum crystal layer to 5 µm or less, preferably 3 µm or less, more preferably 1 µm or less.

In short, in the electrode for electrochemical measurement to be used in an electrochemical analysis apparatus which measures electrochemical response of a chemical component contained in a liquid sample, a valve metal of any of Ti, Ta, Nb, Zr, Hf, V, Mo, and W and platinum are laminated with each other, a cross-sectional crystal texture of the platinum part in the plate thickness direction is formed in a layer-like form with respect to the surface of the electrode, and the thickness of each layer of the platinum part is made to 5 µm or less.

However, the thickness of each layer is preferably set to 0.01 µm or greater since excessive miniaturization of crystal grains causes the material to become harder, resulting in degradation of the processability. The term "layered crystal texture" as used herein refers to the state that the individual crystal texture is elongated with respect to a direction along the electrode plane, that is, stretched in the rolling direction and the state of being compressed in the electrode plate thickness direction. Also, it should be noted that the individual layer is not meant to consist of a single crystal structure; substantially, it consists of a plurality of differently elongated crystal textures. The term "thickness of crystal layer" denotes the length of individual crystal of the platinum part in the plate thickness direction, which can be seen when observing the through-thickness cross-section of a layered electrode of platinum and valve metal.

Incidentally, the individual crystal refers to the texture surrounded by a small-tilt grain boundary with its grain boundary angle of less than 2 degrees. A crystal texture image is observable by electron beam backscatter pattern methods or the like.

For the reason stated above, control of the crystal orientation property of electrode surface as well as the thickness of platinum crystal layer is effective for improvement of the analysis data stability. A preferable plane direction is not specifically limited thereto; electrode with any one of the (111) plane, the (200) plane, the (220) plane, and the (311) plane being preferentially oriented in the X-ray diffraction of platinum surface is preferred. Preferably used is platinum with a prescribed plane direction occupying 80% or more in a peak integration value.

More preferably usable is platinum with its (220) direction being oriented preferentially, which is obtained by fabrication using hot rolling, annealing, and cold rolling in combination. To set the thickness of platinum layer to 5 µm or less, it is performed under the condition that the draft is at 70% or more—preferably, 90% or more—in the process of cold rolling at temperatures lower than or equal to the platinum's recrystallization temperature.

As stated above, concerning the adhesion with the valve metal such as titanium, the surface of titanium or the like reacts with oxygen, carbon, nitrogen, and the like thereby to form an inactive coating and, therefore, it is necessary to expose the metal surface of titanium and to have it rapidly adhere with the platinum. To this end, for example, the inactive coating formed on the titanium surface is removed away by dry etching or the like in a vacuum; thereafter, let it abut on a platinum plate and then undergo forge-welding at temperatures lower than the platinum's recrystallization temperature, thus enabling fabrication of the adhesion.

Alternatively, it is also possible to perform cold rolling after having welded the titanium and the platinum together by known explosive welding methods. It is also permissible to make a cold rolled platinum foil and a titanium plate adhere with each other by explosive welding methods.

Still alternatively, it is also possible to fabricate by joining together a cold rolled platinum foil and a titanium having its surface platinum-plated with their platinum surfaces oppose each other and then performing forging at temperatures lower than the recrystallization temperature. In the case of applying platinum plating to the titanium surface, surface may be treated with a sandblasting method or a chemical etching method as pretreatment for adhesiveness improvement. In the chemical etching method, there may be used a hydrofluoric acid, fluoride-containing hydrofluoric acid, concentrated sulfuric acid, hydrochloric acid, oxalic acid, or a mixed solution of them.

An electrode having a platinum-plated valve metal is also usable. With the control of crystal grain size and orientation property, the platinum plating is enabled by controlling the current density in a plating fluid that contains an organic material as an additive agent. Further, it is also possible to adjust the thickness of platinum crystal layer and the crystal orientation property by performing, after the plating, rolling treatment at temperatures below the recrystallization temperature.

The plate thickness of the valve metal as an underlayer electrode of the multilayer electrode is preferably set at 10 to 5000 μm from a viewpoint of machinability of bending, cutting, or the like although not specifically limited thereto. The thickness of platinum part of the multilayer electrode is preferably 10 to 150 μm. More preferably, the multiplayer electrode's platinum part thickness is 20 to 100 μm.

In the rolling process, a layer having random crystal orientation property may be formed on the top surface layer or a coarse crystal texture is formed due to heat concentration, the depths of which reach about 10 μm from the top layer depending on circumstances. In view of this, the thickness of platinum part is preferably arranged to exceed 10 μm. With a thickness of 150 μm or greater, the amount of platinum becomes larger, resulting in an increase in cost, although it is possible to secure a mechanical strength enough to have no trouble with the electrode being handled alone. Setting the platinum part thickness to 100 μm makes it possible to reduce the platinum amount to thereby lower the cost and to have sufficient mechanical strength free from handling problems because of the multilayer electrode structure.

Preferably, after having fabricated the multilayer electrode by unification of the platinum and the valve metal, mechanical polishing is applied to the platinum electrode surface in a similar way to the event where the metal oxide-dispersed composite material is used. More preferably, the mechanically polished electrode is further subjected to electrolytic polishing.

As with the case of the metal oxide-dispersed composite material being used, the above-stated mechanical polishing and electrolytic polishing are effective processes, especially in the multilayer electrode of platinum and valve metal which was formed by rolling or explosive welding method. Namely, it has been revealed that the crystal orientation property near the surface of an electrode which specifically has experienced hot rolling treatment is relatively random or the plate's inner part and its surface layer part are different from each other in crystal grain size and in orientation property due to local surface heating. While a surface alteration layer formed by such rolling is removed to some extent for the mechanically polished electrode, there still exist the influence of pressure application during the mechanical polishing and scars caused by abrasive particles.

In this manufacturing method of the present invention, the cold rolling causes the inner part of platinum to have crystal orientation property as well; however, it is considered that a surface alteration layer with irregular crystal orientation property is formed near the surface. This is similar to the case of using the metal oxide-dispersed composite material in that the electrolytic polishing is effective on removal of the aforementioned surface alteration layer and can be said to be the process for exposing the metal inside's platinum part having high crystal orientation property.

To determine the degree of removal of the alteration layer on the material surface in the electrode manufacturing process, it is preferable to immerse the above-stated electrode in a prescribed electrolysis solution during electrolytic polishing and diagnose its surface state by means of cyclic voltammetry. Namely, from the results of this cyclic voltammetry a plurality of hydrogen absorption/desorption current peaks can be obtained. These current peaks become current amounts depending on the plane directions of the electrode surface and thus may serve as the criterion for determining the degree of removal of a surface alteration layer created by rolling and mirror-polishing processes.

Areas of at least two of the obtained peaks are calculated along with an area ratio thereof. Based on such calculation results, electrolytic polishing is carried out until a prescribed area ratio is reached, thereby making it possible to obtain the electrode with the surface alteration layer removed away.

Incidentally, examples of the electrolytic solution used in the cyclic voltammetry include sulfuric acid, phosphoric acid, hydrochloric acid, perchloric acid, sodium hydroxide, potassium hydroxide, and aqueous ammonia.

A counter electrode for use in an electrolysis cell may be appropriately chosen in accordance with the liquid sample under analysis; platinum or a platinum alloy is employable. The electrode of the present invention may also be used as the counter electrode. Examples of its shape include, but not limited to, a wire-like shape, a rod-like shape, a mesh-like shape, and a plate-like shape.

A reference electrode used in an electrolysis cell may be a silver|silver-chloride electrode, a saturated calomel electrode, a silver electrode, or the like, although not specifically limited thereto.

It was revealed that the electrolysis cell and an analysis apparatus using the above-stated metal oxide-dispersed composite material as their working electrodes are such that their electrochemical responses are less in variation of electrode surface state over an extended period of time and also less in change in exposed crystal orientation property, thus showing stable measurement results. In the case of placing the working electrode in a flow cell, it also becomes possible to suppress formation of the electrode surface state—in particular, local dents in the electrode plane—for a prolonged time period to thereby stably perform the liquid substitution of an analyte liquid and a cleaning fluid, resulting in improvement of data stability.

It was also found that the analysis apparatus using as its working electrode the above-stated electrode with platinum and valve metal unified and multilayered is less in variation of electrochemical response over a long time and exhibits stable measurement results. In the case of placing the working electrode in a flow cell, the electrode is also less in variation of its surface area over a long time and also less in variation of surface irregularity; thus, it becomes possible to stably implement the substitution of an analyte liquid and a cleaning fluid, resulting in improvement of data stability.

Additionally, in the electrochemical analysis apparatus including the flow cell, when using as the working electrode an electrode that was formed by a manufacturing process including rolling treatment, it is preferable to place it in such a manner that the electrode's rolling direction forms an angle with the flow direction of a liquid sample of 45 to 135 degrees. Regarding the analytic substance, in the case of analyzing the electrochemical response of a chemical component adsorbed, for example, to magnetic beads or the like, if the rolling direction is the same as the flowing direction, then the beads tend to readily flow from the working electrode while being analyzed, resulting that data tend to vary. In cases where the rolling direction is less than 45 degrees or exceeds 135 degrees with respect to the flow direction, the aforementioned influence can take place in no small extent. It was found that when the electrode is disposed so that the rolling direction falls within a range of 45 to 135 degrees with respect to the flow direction in angle, a step produced between crystal textures thereof—though this is tiny irregularity—causes magnetic beads with their sizes of submicrons to several μm, for example, to easily reside on the working electrode surface, resulting in an ability to improve the data stability.

By using the electrode, the electrolysis cell, and the electrochemical analysis apparatus of the present invention, it is possible to analyze a chemical component contained in a liquid sample such as blood, urine, or the like, examples of which component are shown below.

That is to say, some of such examples are glucose, glycosylated hemoglobin, glycosylated albumin, lactic acid, uric acid, urea, creatinine, bile acid, cholesterol, neutral fat, ammonia, urea nitrogen, bilirubin, and histamine. Note, however, that these are not limited thereto as far as they are components which exhibit the electrochemical response of redox species occurred by the action of enzyme, mediator, or the like. Also analyzable are components to be subjected to electrochemical measurement after having captured the target component on the electrode surface using magnetic particles having their surfaces modified by a component selectively connecting with the chemical component being analyzed.

On occasions when detecting the glucose, the concentration of it is quantitatively determined by on-electrode reduction or oxidation of hydrogen peroxide, which was produced by letting glucose oxidase act thereon by way of example.

When detecting the glycosylated protein such as glycosylated hemoglobin or glycosylated albumin, it is possible to quantify the concentration of glycosylated protein by releasing glycosylated peptide from the glycosylated protein with protease, for example, and then reducing or oxidizing on the electrode a hydrogen peroxide which was produced by letting glycosylated peptide oxidase act thereon.

When detecting the lactic acid, its concentration is quantifiable, for example, by reducing or oxidizing on the electrode a hydrogen peroxide that was produced by letting lactate oxidase act thereon.

When detecting the uric acid, its concentration is quantifiable, for example, by reducing or oxidizing on the electrode a hydrogen peroxide produced by letting uricase act thereon.

When detecting the urea, its concentration is quantifiable, for example, by oxidizing on the electrode a potassium ferrocyanide produced by causing glutamate dehydrogenase to act on ammonia produced by letting urease act thereon, in the presence of β-nicotinamide adenine dinucleotide (NADH) and potassium ferricyanide.

When detecting the creatinine, its concentration is quantifiable, for example, by reducing or oxidizing on the electrode a hydrogen peroxide that was produced by causing creatininase, creatinase, and sarcosine oxidase to act thereon sequentially.

When detecting the bile acid, its concentration is quantifiable, for example, by oxidizing on the electrode a potassium ferrocyanide that was produced by causing bile-acid sulfuric-acid sulfatase and β-hydroxysteriod dehydrogenase to sequentially act thereon in the presence of reduction-type NADH and potassium ferricyanide.

When detecting the cholesterol, its concentration is quantifiable, for example, by reducing or oxidizing on the electrode a hydrogen peroxide produced by letting cholesterol oxidase act thereon.

When detecting the neutral fat, its concentration is quantifiable, for example, by reducing or oxidizing on the electrode a hydrogen peroxide produced by letting glycerophosphate oxidase act thereon.

When detecting fatty acid, its concentration is quantifiable, for example, by reducing or oxidizing on the electrode a hydrogen peroxide produced by letting acyl-CoA oxidase act thereon.

When detecting the ammonia, its concentration is quantifiable, for example, by oxidizing on the electrode a potassium ferrocyanide produced by letting glutamate dehydrogenase act thereon in the presence of NADH and potassium ferricyanide.

When detecting the bilirubin, the concentration of urea nitrogen is quantifiable, for example, by oxidizing on the electrode a potassium ferrocyanide that was produced by letting bilirubin oxidase act thereon in the presence of potassium ferricyanide.

The above-described enzyme and the like are immobilized on a surface of the electrode. Examples of the methodology of fixing the enzyme and the like to the electrode surface include, but not limited to, a method for immersing the electrode in either an aqueous solution of the enzyme and the like or a buffer fluid and a method of causing an aqueous solution of the enzyme and the like or a buffer fluid to fall onto the electrode to thereby immobilize the enzyme physically or chemically. Another example is a method for immersing the electrode in a solution containing thiol with a functional group such as a carboxyl group or an amino group introduced into the end group so that aforementioned thiol is adsorbed onto the electrode surface and then for letting the enzyme or the like react therewith to thereby perform immobilization. Further examples are a method for immobilizing the enzyme or the like on the electrode by using either a cross-linking reagent such as glutaraldehyde or by further using bovine serum albumin, a method for forming on the electrode a film of gel such as hydrophilic macromolecules and then fixing the enzyme or the like in this film, and a method for forming on the electrode an conductive polymeric film such as polythiophene and then fixing the enzyme or the like therein.

Upon detection of the object to be analyzed, it is effective to utilize mediator molecules, as the need arises, in order to extend the range of detected concentration. In the case of using mediator molecules, it is preferable to place the mediator molecules on the electrode in an immobilization film of biologically active substance of the enzyme and the like formed on the electrode or separately therefrom. Kinds of the mediator molecule include are not particularly limited but at least one of potassium ferricyanide, potassium ferrocyanide, ferrocene and its derivative, viologen and the like, methyleneblue, and the like can be used.

Next, an explanation will be given of embodiments of the present invention based on the above-stated principles.

Embodiment 1

Explained below is an overall arrangement of an electrochemical analysis apparatus in accordance with one embodiment of the present invention using an electrode in accordance with one embodiment of this invention.

FIG. 1 shows an entire configuration of an electrochemical analysis apparatus in accordance with Embodiment 1 of the present invention. Embodiment 1 of this invention is an electrochemical analyzer having the form of a batch processing scheme.

In FIG. 1, an electrolysis cell 1 has a working electrode 2, a counter electrode 3, and a reference electrode 4 which are disposed therein. Respective electrodes 2, 3, 4 are connected by lead wires 7 to an electric potential-applying means 5 and a measuring means 6. The counter electrode 3 used here is the one that was obtained by rolling platinum into a plate-like shape and then mechanically polishing its surface. The reference electrode 4 was an Ag|AgCl electrode. Note here that in this description, the silver|silver-chloride (saturated potassium chloride aqueous solution) electrode is denoted by Ag|AgCl.

A solution-dispensing mechanism 11 introduces into a solution inlet pipe 13 an analyte solution that contains a chemical component under measurement from an analyte solution vessel 8 and a buffer fluid from a buffer fluid vessel 9, respectively. The solution under measurement and the buffer fluid thus introduced are mixed together in the solution inlet pipe 13 and the mixed solution is injected by a solution injection mechanism 12 into the electrolysis cell 1, thereby performing electrochemical measurement of the object to be assayed.

As for the potential applying means 5 a potentiostat, a galvanostat, a DC power supply, an AC power supply, or a system with one of them being connected to a function generator or the like can be used. The measuring means 6 measures electrochemical characteristics of the object assayed. Incidentally, the electrochemical characteristics may be any one of known measurement schemes such as potentiometry, amperometry, voltammetry, and impedance measurement although not specifically limited thereto. Others include a method for detecting, by an optical element, photons to be produced in accordance with electrochemical reaction.

The measurement-completed solution is sucked by a solution exhaust mechanism 15 and then discarded to a waste container 16 through a solution outlet pipe 14. After completion of the measurement of a sample, a cleaning liquid is inhaled by the solution-dispensing mechanism 11 from a cleaning liquid vessel 10 and then supplied by the solution injection mechanism 12 into the electrolysis cell 1. The cleaning liquid that rinsed the interior of the electrolysis cell 1 is discarded to the waste container 16.

Here, as a typical example, the voltage applying means 5 outputs to the working electrode during measurement of the to-be-measured solution a voltage having a pulse-like waveform with positive and negative potentials being repeated in a prescribed cycle. This pulse-like waveform potential is arranged to be applied on occasions when continuously flowing in the electrolysis cell a measurement solution that contains large amounts of protein and halogen element such as blood for a long time period or when flowing a cleaning agent of a strong alkali such as potassium hydroxide into the measurement vessel. Although in this Embodiment 1 the above-noted potential application waveform was used, this invention is not specifically limited thereto.

Here, an electrode material used for the working electrode 2 is a composite material with zirconium oxide being dispersed in platinum. The aforementioned composite material was fabricated in accordance with a fabrication method which follows. A platinum-0.2% zirconium alloy was subjected to vacuum fusion, thus forming an ingot. Subsequently, after forging treatment, the aforementioned ingot was rolled to thereby perform wiredrawing processing. This wiredrawn one was fused and sprayed by a flame gun toward a distilled water bath, thereby obtaining a platinum alloy powder. The obtained platinum alloy powder was held in the air at 1250° C. for 24 hours; then, oxidation processing was applied thereto. The oxidized alloy powder is temporarily sintered at 1250° C. and then molded and solidified by a hot press. To improve the degree of compactness, the molded body is subject to hot forging. Finally, this alloy was cold rolled with a draft of 90% and heated at 1400° C. for 1 hour, thereby obtaining a plate-shaped composite material with a plate thickness of 0.2 mm.

The above-stated composite material was used to fabricate the working electrode 2 in a procedure which follows.

Figure 2:
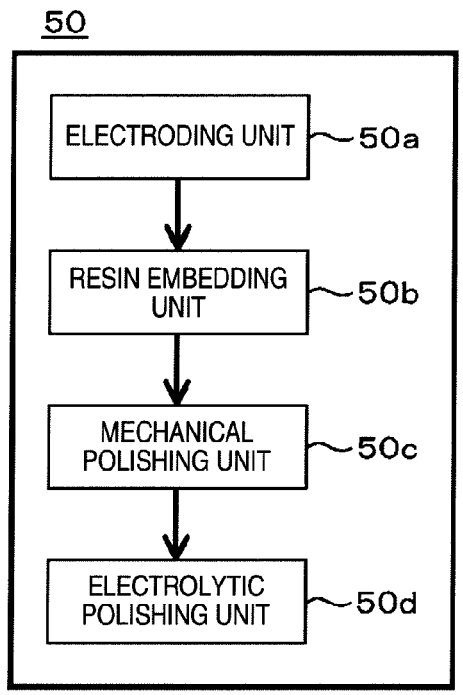
FIG. 2 is a schematic configuration diagram of an electrode manufacturing apparatus for electrode for an electrochemical measurement apparatus in accordance with one embodiment of the present invention.

The aforementioned composite material was cut into a size of 5 mm in diameter. Thereafter, by a working electrode manufacturing apparatus 50 shown in FIG. 2, a lead wire 302 was first connected by soldering to the back surface of composite material 301 that has been cut at an electroding unit 50a. A dielectric resin-coated copper line was used as the lead wire.

Next, at a resin embedding unit 50b, an adhesive agent 303 was used to embed it in an insulative resin 300 in such a way that only the composite electrode's surface is exposed at a portion having a circular shape with a diameter of 5 mm. As the dielectric resin, a fluorine-based resin was used.

Next, at a mechanical polishing unit 50c, the electrode surface was mechanically polished by sequentially using water-proof abrasive paper, diamond paste, and alumina particles, thereby causing it to have a mirror-finished surface.

Next, a stainless-steel shaft 304 was screwed into the fluorine-based resin, thereby connecting the shaft 304 and the lead wire 302 with each other. Finally, at an electrolytic polishing unit 50d, electrical potential scanning was repeated 10,000 times between potential levels of −1.2 to 1.0V vs. Ag|AgCl in a 0.2 mol/L potassium hydrate aqueous solution at a potential scanning rate of 0.1 V/s, thus obtaining the working electrode 2 shown in FIG. 3. Note that FIG. 4 is a schematic cross-sectional diagram taken along line A-A' of FIG. 3.

Figure 5:
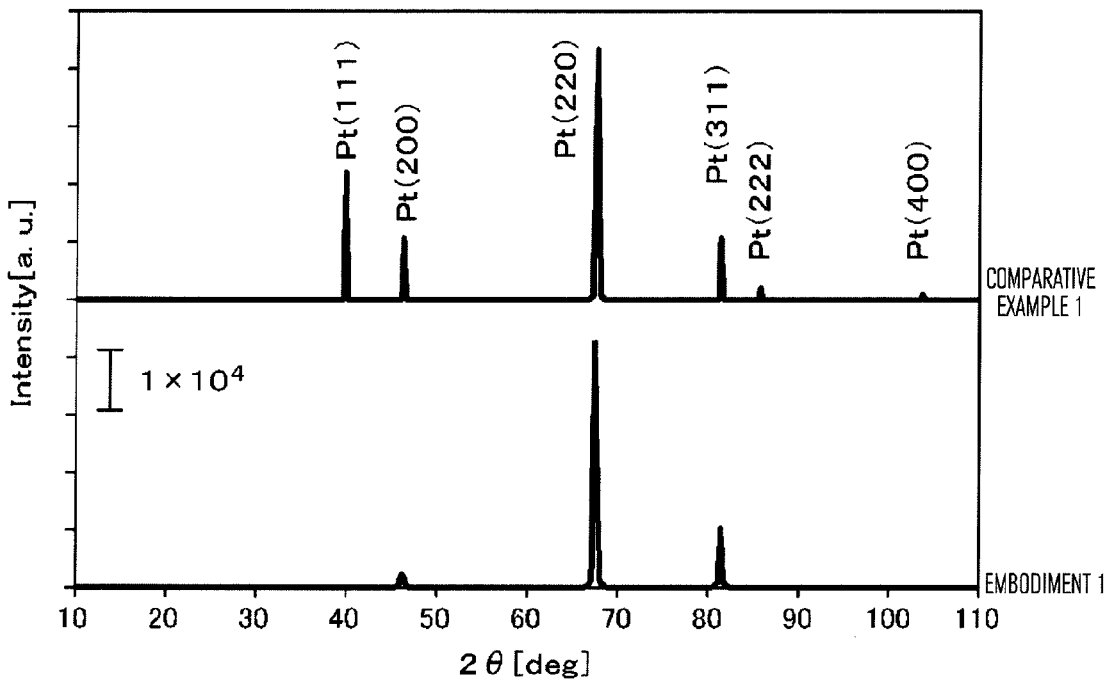
FIG. 5 shows X-ray diffraction analysis results of electrodes of one embodiment of the present invention and one comparative example.

X-ray diffraction measurement was performed of the electrode surface of the working electrode 2 fabricated in the present Embodiment 1. CuKα was used as an X-ray source to measure three different points on the electrode surface with output settings of 40 kV and 20 mA. Integration values (I) of diffraction peaks of a (111) plane, a (200) plane, a (220) plane, and a (311) plane on the platinum surface were calculated to thereby obtain each direction's orientation ratio ((%)=I(hkl)/ΣI(hkl)×100). Incidentally, the calculation of each peak integration value was done in the ranges of $37°≤2θ≤42°$ for the (111) plane, $44°≤2θ≤49°$ for the (200) plane, $65°≤2θ≤70°$ for the (220) plane, $78°≤2θ≤83°$ for the (311) plane, respectively (where θ is the diffraction angle). As results of the measurement, as shown in FIG. 5, it was revealed that the plane index (220) is preferentially oriented with its orientation ratio of 95%.

Figure 6:
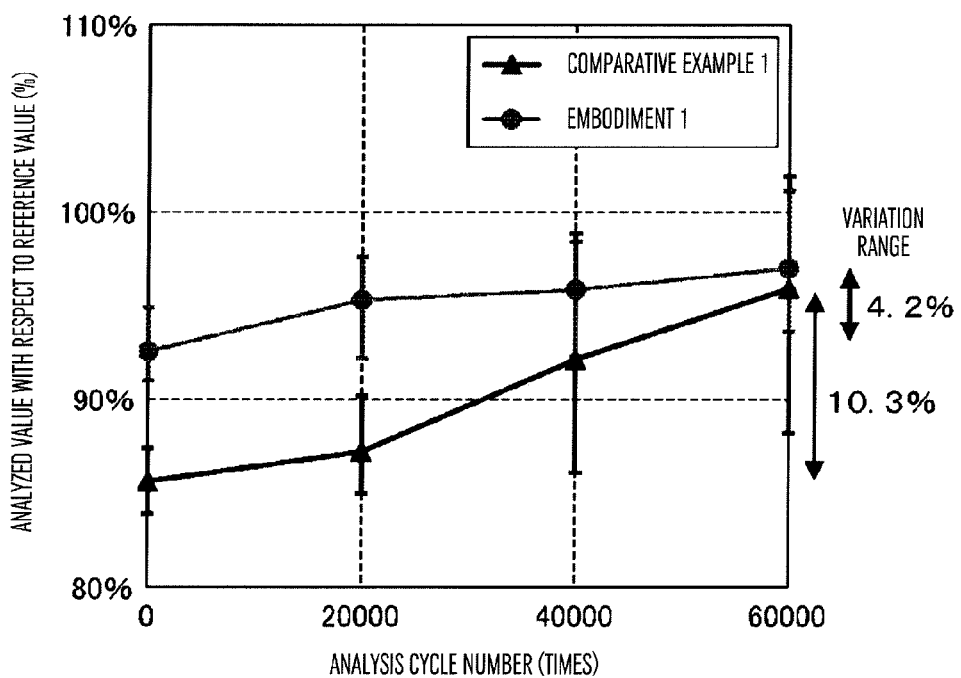
FIG. 6 is a diagram for explanation of effects of an electrode based on one embodiment of the present invention.

FIG. 6 is a diagram for explanation of the effect of a metal oxide-distributed platinum electrode employed in Embodiment 1 of the present invention. Measurement was repeatedly performed with TSH (thyroid stimulating hormone) of the same concentration as an analyte. The abscissa of FIG. 6 designates the number of times of testing whereas the ordinate indicates the value of each actual measurement value divided by a reference value. The reference value is an output value upon measurement of a TSH-containing solution with a prescribed concentration; the actual measurement values are measured values when respective solutions used in Embodiment 1 and Comparative Example 1. The variation range is defined as a difference between values obtained in the sixty-thousandth test and in the first test. In FIG. 6, lines connecting circular marks are in the case of this Embodiment 1 and line connecting triangular marks are in the case of Comparative Example 1 different from the present invention.

Figure 3:
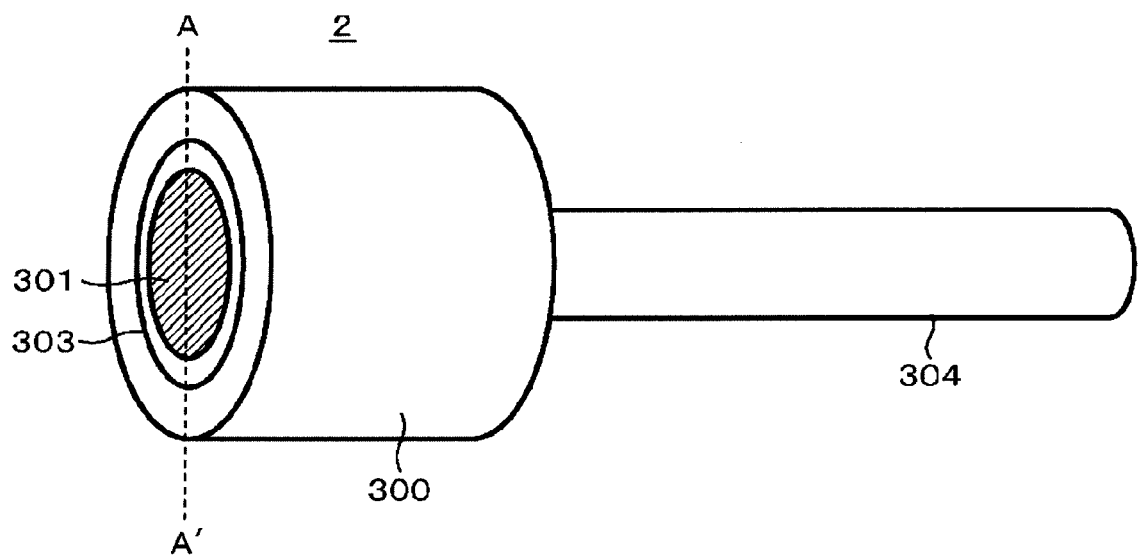
FIG. 3 is a configuration diagram of an electrode used for electrochemical measurement in accordance with one embodiment of the present invention.
Figure 4:
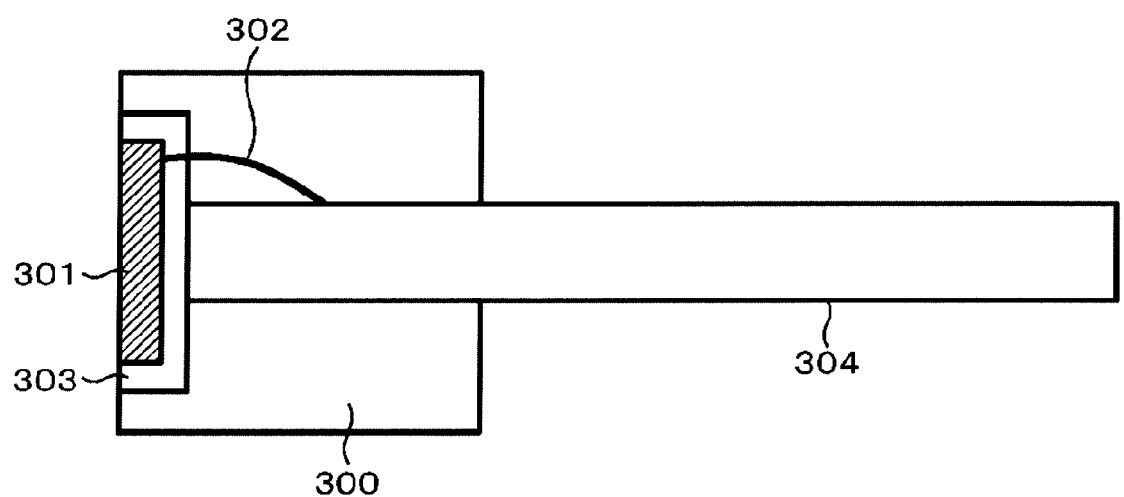
FIG. 4 is a diagram showing a cross-sectional structure along A-A' plane of FIG. 3.

The electrode of FIG. 3 and the electrochemical analyzer of FIG. 1 were used to perform measurement in a method for immunologically analyzing a TSH in blood serum as the measurement solution and for introducing potassium hydroxide aqueous solution, for example, as a cleaning liquid into the electrolysis cell once per completion of each measurement.

As shown in FIG. 6, the variation range in the case of using an electrode of Comparative Example 1 was 10.3%. The electrode of Comparative Example 1 is a platinum electrode to which hot rolling and recrystallization processing were applied and to a platinum surface of which mechanical polishing and electrolytic treatment were applied. Details will be explained in the context of comparative examples to be described later. On the other hand, in the case of using the electrode of the present Embodiment 1, the variation range was reduced to 4.2%.

The electrode of this Embodiment 1 is a platinum electrode in which zirconium oxide was dispersed as a metal oxide. The contained amount of zirconium in this electrode is 0.2% in the metal-equivalent value, wherein a surface alteration layer that was created during the rolling and mechanical polishing processes is removed away and wherein it is preferentially oriented in the plane direction (220) at an orientation ratio of 80% or more. In the analyzer using this electrode as its working electrode, the etching rate difference within the electrode surface is small so that advantageous effects were ascertained that non-uniform in-plane dissolution is suppressed and the crystal orientation property of crystals exposed to the top surface is small in change even when the analysis is repeated so that it becomes possible to reduce variations of the surface state and a fluctuation in the electrochemical response is small over a long period, thus making it possible to obtain stable measurement results.

Figure 7:
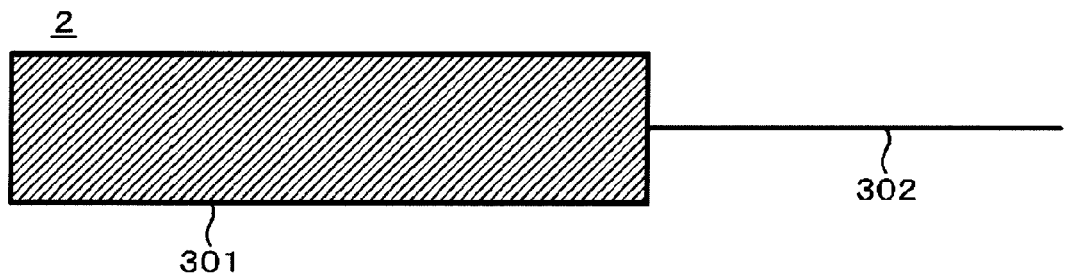
FIG. 7 is a configuration diagram of an electrode for electrode for electrochemical measurement in accordance with one embodiment of the present invention.
Figure 8:
FIG. 8 is a configuration diagram in the case of viewing from a side face of FIG. 7.

While in Embodiment 1 the electrode with composite material buried in fluorine resin was used, a metal oxide-dispersed composite material is used as the electrode and this electrode exhibits an effect on the data stability. So, this invention is not specifically limited to any form. For example, it was made sure that similar effects are also obtainable in the case of a plate-like form where it is not buried in resin as shown in FIG. 7, for example (FIG. 8 is a side view of FIG. 7).

Embodiment 2

Figure 9:
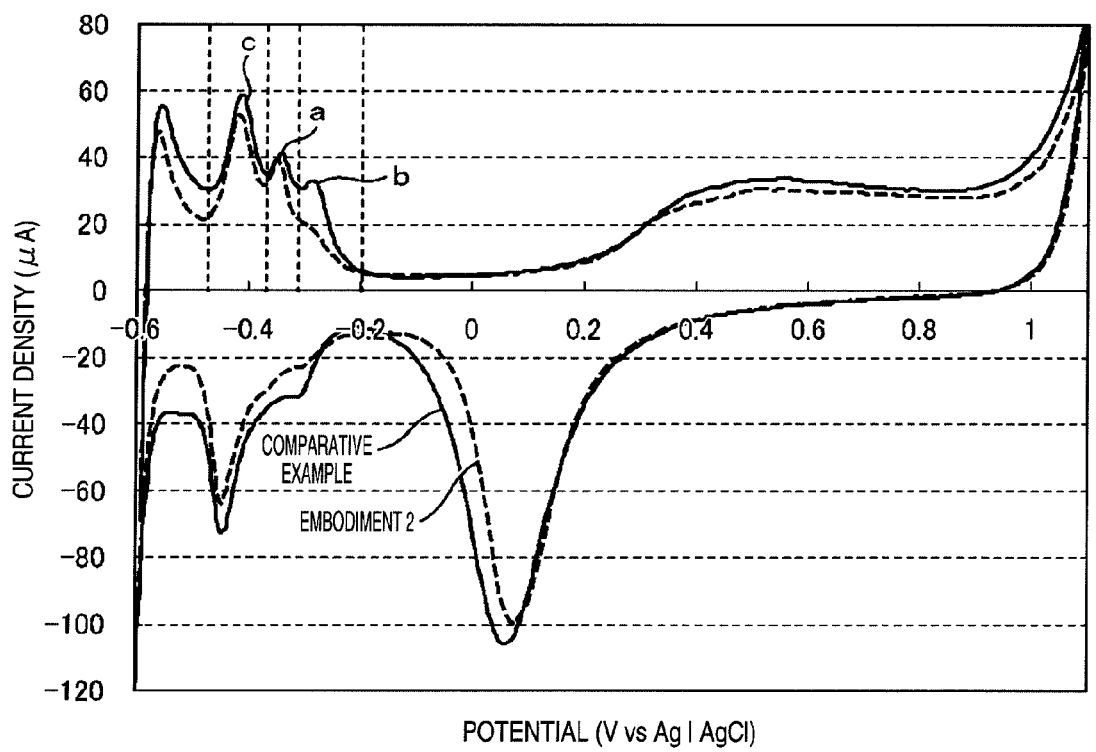
FIG. 9 is a cyclic voltammogram of electrodes of one embodiment of the present invention and one comparative example.

Embodiment 2 of the present invention will be set forth next. An electrode and an electrochemical analysis apparatus using it are similar to those of Embodiment 1 except that in the manufacture of an electrode, the electrode is immersed in a prescribed electrolysis solution during electrolytic polishing, and a surface alteration layer on the electrode surface is removed while at the same time conducting diagnosis on the surface state by cyclic voltammetry. The cyclic voltammetry was performed using a nitrogen-substituted phosphoric acid buffer fluid at a pH of 6.86 as the electrolytic solution under the condition of a potential scan range of from −0.6 to 1.1 V and a scan rate of 0.1 V/s while letting its working electrode be the working electrode 2, letting its counter electrode be a platinum wire, and letting its reference electrode be Ag|AgCl. A measurement result is shown in FIG. 9. Incidentally, for comparison purposes, a result of Comparative Example 1 is also shown. Among a plurality of hydrogen absorption/desorption current peaks obtained from the results of cyclic voltammetry, letting "a" to be a peak observed in a range of −0.37 to −0.31 V and "b" to be a peak seen in a range of −0.31 to −0.2 V, their peak areas and an area ratio b/a are calculated. Electrolytic treatment was performed until the area ratio becomes 80% or less; thus, the working electrode 2 was obtained.

As a result of repeated execution of analysis by the electrochemical analyzer using the working electrode in accordance with Embodiment 2 of the present invention in a similar way to Embodiment 1, an excellent result was obtained showing that the variation range is 3.8%. As a result of X-ray diffraction analysis of the electrode, it was revealed that it is preferentially oriented in the (220) direction with an orientation ratio of 96%. In the analyzer using this electrode as its working electrode, the etching rate difference within the electrode surface is small so that advantageous effects were ascertained that non-uniform in-plane dissolution is suppressed and the crystal orientation property of crystals exposed to the top surface is small in change even when the analysis is repeated so that it becomes possible to reduce variations of the surface state and a fluctuation in the electrochemical response is small over a long time, thus making it possible to obtain stable measurement results.

Although in Embodiment 2 of this invention the peaks a and b are used as the criterion for judgment of the degree of surface alteration layer removal, it was ascertained that similar results are also obtainable by calculating a ratio b/c from the peak c seen in the range of −0.48 to −0.37 V and the peak b and for letting b/c be 35% or less as the criterion.

Embodiment 3

Figure 10:
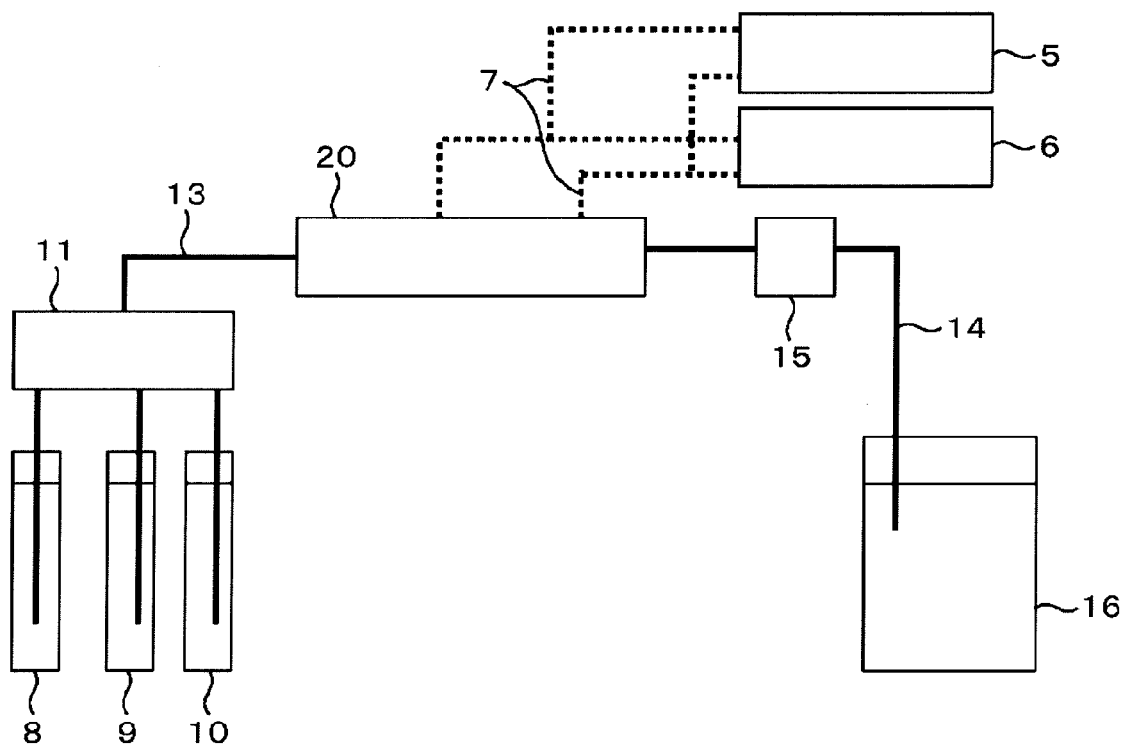
FIG. 10 is an overall configuration diagram of an electrochemical analysis apparatus in accordance with one embodiment of the present invention.

An electrochemical analysis apparatus in accordance with Embodiment 3 of the present invention will be explained using FIG. 10, FIG. 11A, and FIG. 11B. FIG. 10 is a schematic configuration diagram of the electrochemical analyzer in Embodiment 3 of this invention. In addition, FIG. 11A is an exploded configuration diagram of a flow cell for use in the electrochemical analyzer shown in FIG. 10, and FIG. 11B is its assembly cross-section diagram.

The example shown here in FIG. 10 is similar to that shown in FIG. 1 except that the electrolysis cell 1 shown in FIG. 1 is replaced with a flow cell 20 in FIG. 10.

Figure 11A:
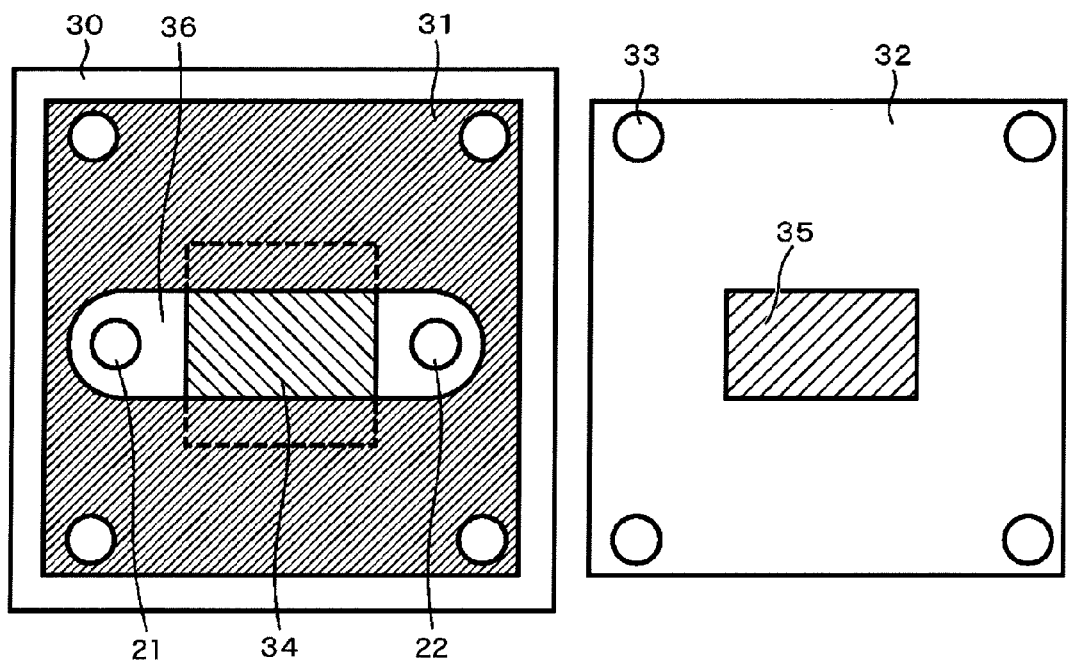
FIG. 11A is an exploded configuration diagram of a flow cell used for an electrochemical analysis apparatus in accordance with one embodiment of the present invention.
Figure 11B:
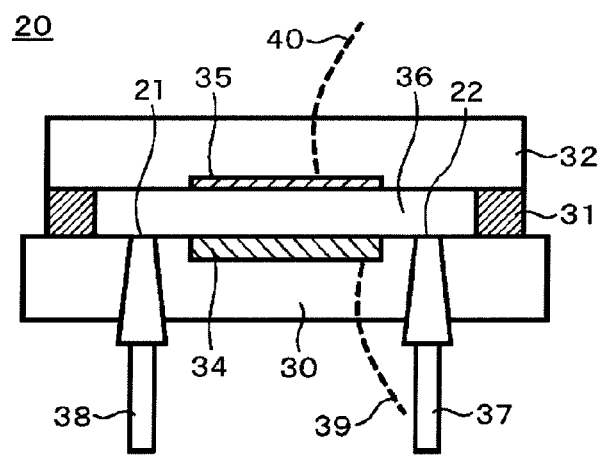
FIG. 11B is a cross-sectional assembly diagram of the flow cell used for an electrochemical analysis apparatus in accordance with one embodiment of the present invention.

In FIG. 11B, the flow cell 20 serving as an electrolysis cell was formed by laminating two electrically insulative substrates 30 and 32 and a sealing member 31 shown in FIG. 11A in a way shown in FIG. 11B. As the insulative substrate 30 polyether ether ketone was used. On one face of the insulative substrate 30, a working electrode 34 is fastened. Here, an electrode material used for the working electrode 2 was a composite material with zirconium oxide dispersed in platinum. The composite material was fabricated by a manufacturing method which follows. A suspension liquid with platinum powder of the particle diameter of 5 μm and calcium carbonate mixed together was subjected to ball-mill processing, this suspension was heat-treated at a high temperature of 1100° C., and, after having immersed the bulk obtained by such high-temperature heat-treatment into water, nitric acid treatment was performed. 2 kg of the obtained platinum powder was put into 4 L of pure water, thereby producing a platinum suspension liquid. This platinum suspension was mixed with 9 g of zirconium nitrate solution and agitated at room temperature for about 3 minutes; thereafter, 2.0 g of ammonia aqueous solution was added for adjustment to a pH of 7.5 and filtering collection from the mixed liquid was performed, thus obtaining a zirconium hydroxide-supporting platinum powder. The collected zirconium hydroxide-holding platinum powder was rinsed and dried at 120° C. in the atmospheric air. Subsequently, this zirconium hydroxide-holding platinum powder was forced to pass through a sieve with an aperture size of 300 μm. This zirconium hydroxide-holding platinum powder was filled into a vessel and cold-molded at a pressure of 100 MPa, thereby obtaining a molded body. This molded body was sintered in the air at 1200° C. for 1 hour and then forged using an air hummer, thereby obtaining a platinum ingot with zirconium oxide dispersed therein. Cold rolling was applied to this ingot in which the draft became 90%. Subsequently, recrystallization heating was performed at 1400° C. for 1 hour whereby a composite material with a plate thickness of 150 μm was fabricated. In the composite material obtained, zirconium oxide was contained by about 0.1% in the metal-equivalent value. Incidentally, the concentration of zirconium contained in the composite material was assayed by inductively-coupled plasma mass spectrometry (ICP-MS) after having resolved the material by aqua regia.

Figure 16:
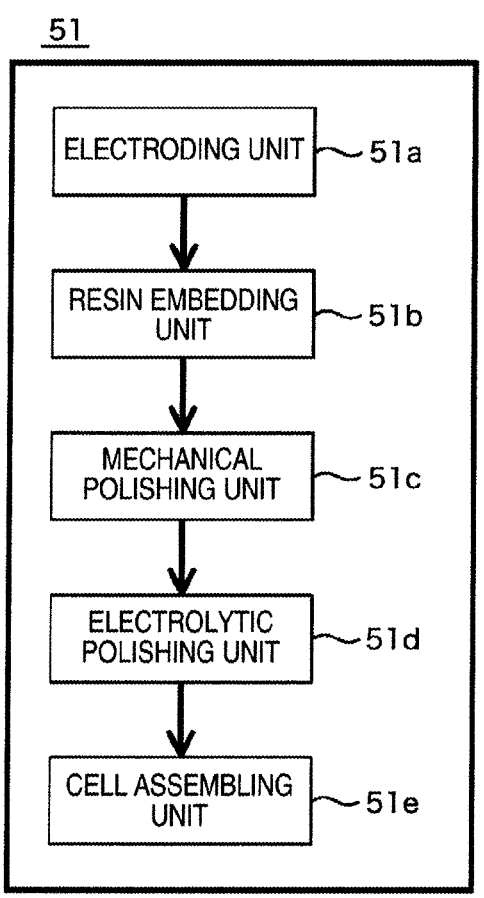
FIG. 16 is a schematic configuration diagram of an electrolysis cell manufacturing apparatus in accordance with one embodiment of the present invention.

The insulative substrate 30 with the immobilized working electrode 34 was fabricated in accordance with a production flow shown in FIG. 16.

At an electroding unit 51a, an insulative resin-coated aluminum wiring lead 39 was connected by soldering to the above-stated composite material whereby a working electrode 34 was obtained. Next, at a resin embedding unit 51b, it was embedded into a depression portion provided in advance in the surface of the insulative substrate 30 and, then, fixed with an adhesive agent. Thereafter, at a mechanical polishing unit 51c, mechanical polishing was performed using waterproof abrasive paper, diamond paste, and alumina sequentially until a step-like surface difference between the insulative substrate 30 and the electrode disappears, thereby obtaining a mirror-finished surface. Thereafter, at an electrolytic polishing unit 51d, application of electrical potential with rectangular pulses of −1.2 V/0.5 sec and 3.0 V/1.5 sec was repeated 10,000 times in 0.2 mol/L potassium hydroxide aqueous solution. The obtained working electrode 34 has its surface with Ra (arithmetic mean roughness) of about 0.6 μm. Finally, at a cell assembling unit 51e, an electrolysis cell 20 was formed by laminating the seal member 31 and the insulative substrate 32.

The insulative substrate 32 is formed by a substrate made of transparent dielectric resin. A counter electrode 35 is fixed to one surface (the surface on the side opposing the electrically insulative substrate 30) of the insulative substrate 32. The counter electrode 35 used here is the one that was annealed at 1000° C. for 1 hour after having machined the platinum into the shape of the electrode.

In the surface of the electrically insulative substrate 32, a depression portion is formed; in this depression portion, the annealed counter electrode 35 is buried and bonded by an adhesive agent and, then, the surface of the counter electrode 35 was mirror-polished. Incidentally, the shape of the counter electrode 35 is not limited to the plate-like shape and may alternatively be of a comb-like shape, a mesh-like shape, or a rod-like shape. Also, the electrode material is not limited to platinum and may also be other platinum-group metals. The counter electrode 35 may be made of platinum to which electrolytic polishing was applied after the mirror polishing in a similar manner to the working electrode 34.

The working electrode 34 and the counter electrode 35 are connected by soldering to lead wires 39 and 40 prior to being embedded in the insulative substrates 30 and 32, respectively, and the lead wires 39, 40 are arranged to run through holes made in the insulative substrate 30, 32.

The seal member 31 is made of fluorine-based resin and has an opening 36 at its center. In the insulative substrate 30, holes 21 and 22 for coupling with pipes 37 and 38 are formed with the working electrode 34 being placed therebetween; these two holes 21 and 22 are disposed to lie within the opening 36, thereby making it possible to take a solution into and out of the opening 36. The working electrode 34 and the counter electrode 35 oppose each other via the opening 36 of the seal member 31.

At four corners of the insulative substrates 30, 32 and the seal member 31, screw holes 33 are formed, through which screws are put respectively to cramp and fasten the insulative substrate 30, the seal member 31, and the insulative substrate 32 together, thereby forming the flow cell 20.

In the insulative substrate 30, pipes 37 and 38 made of fluororesin are fixed and connected to a surface on the side opposite to the surface on which the working electrode 34 is placed. As will be described later, one of the pipes 37 and 38 is connected to a mechanism for introducing a solution under measurement or the like into the flow cell 20; the other is used as a flow path for exhausting the measurement-completed solution. Besides, a reference electrode (not shown in FIG. 11B) is disposed at a pipe 38, that is a part of the solution exhaust-side pipe, and is used as a reference electrode in the event of applying a potential to the working electrode.

Incidentally, the flow cell of the present invention is not specifically limited to the embodiment shown in FIG. 11A and FIG. 11B and may be arranged to have other arrangements. Some exemplary flow cells with other arrangements will be explained below.

Figure 12A:
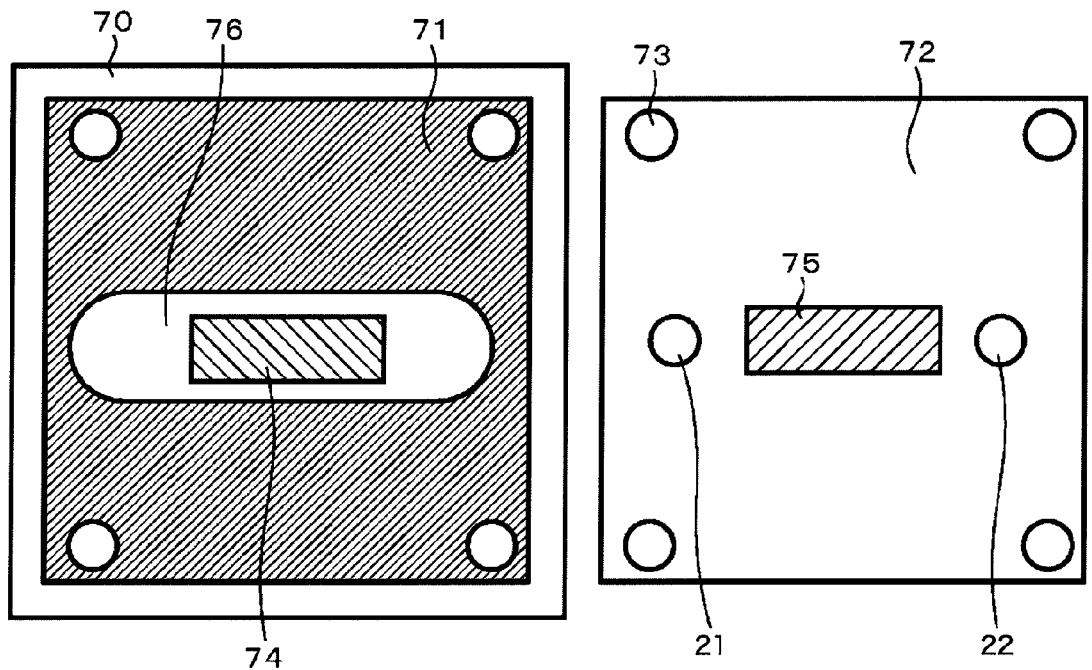
FIG. 12A is an exploded configuration diagram of another example of the flow cell used for an electrochemical analysis apparatus of an embodiment of the present invention.
Figure 12B:
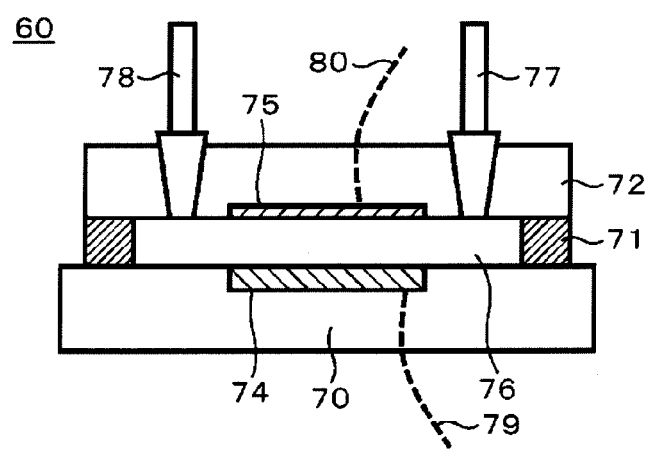
FIG. 12B is a cross-sectional assembly diagram of another example of the flow cell used for an electrochemical analysis apparatus of an embodiment of the present invention.

FIG. 12A and FIG. 12B are diagrams showing another example of the flow cell. In FIG. 12B, a flow cell 60 is formed by laminating respective members shown in FIG. 12A, that is, two electrically insulative substrates 70 and 72 and a seal member 71 in a manner shown in FIG. 12B. Secured to one surface of the insulative substrate 70 (the surface opposing the electrically insulative substrate 72) is a working electrode 74. A counter electrode 75 is fixed to one surface of the insulative substrate 72 (the surface opposing the electrically insulative substrate 70).

The working electrode 74 and the counter electrode 75 are connected by soldering to lead wires 79 and 80 before being embedded in the insulative substrates 70 and 72, respectively, and the lead wires 79, 80 are arranged to run through holes made in the insulative substrates 70, 72, respectively.

At the center of the seal member 71 an opening 76 is formed. In the insulative substrate 72, holes 21 and 22 for coupling with pipes 77 and 78 are formed with the counter electrode 75 being positioned therebetween; these two holes 21 and 22 are disposed to lie within the opening 76, thereby making it possible to take a solution into and out of the opening 76. The working electrode 74 and the counter electrode 75 oppose each other via the opening 76 of the seal member 71.

At four corners of the insulative substrates 70, 72 and the seal member 71, screw holes 73 are formed, through which screws are put respectively to thereby cramp and fasten the insulative substrate 70, the seal member 71, and the insulative substrate 72 together, thereby forming the flow cell 60.

In the insulative substrate 72, pipes 77 and 78 made of fluororesin are fixed and connected to a surface on the opposite side to the surface on which the counter electrode 75 is provided. One of the pipes 77 and 78 is coupled, as will be described later, to a mechanism for introducing a solution under measurement or the like into the flow cell 60; the other is used as a flow path for exhausting the measurement-completed solution.

Beside, a reference electrode (not shown in FIG. 12B) is placed at a solution exhaust-side pipe section and used as a reference electrode when applying a potential to the working electrode 74.

Figure 13A:
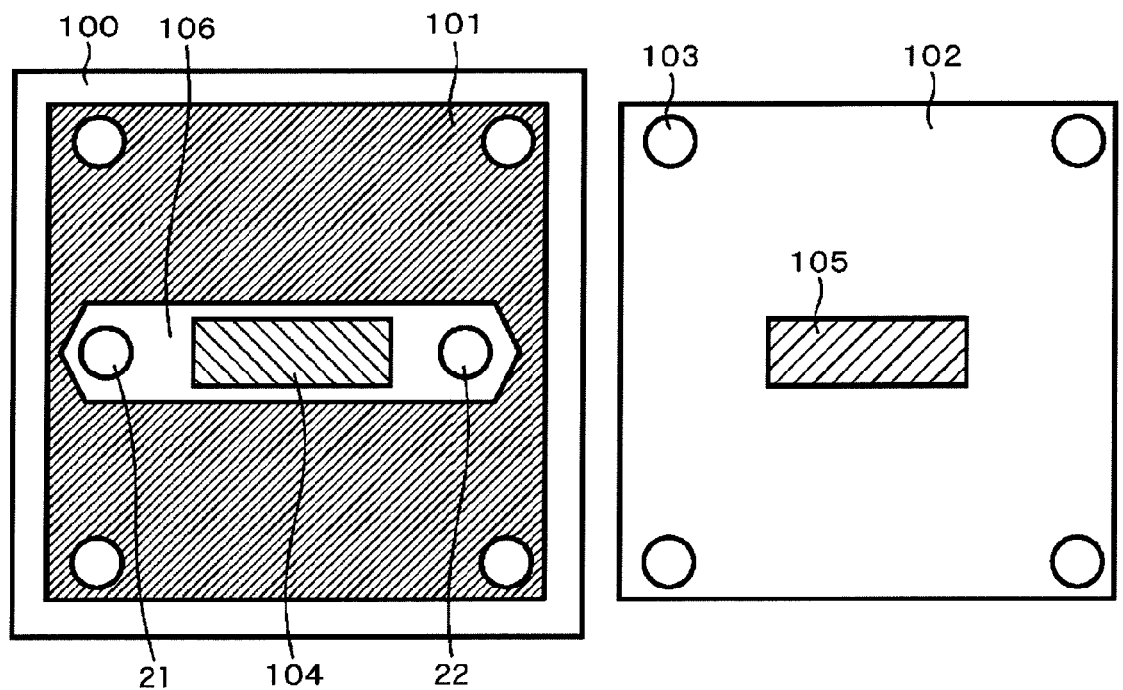
FIG. 13A is an exploded configuration diagram of a further example of the flow cell used for an electrochemical analysis apparatus of an embodiment of the present invention.
Figure 13B:
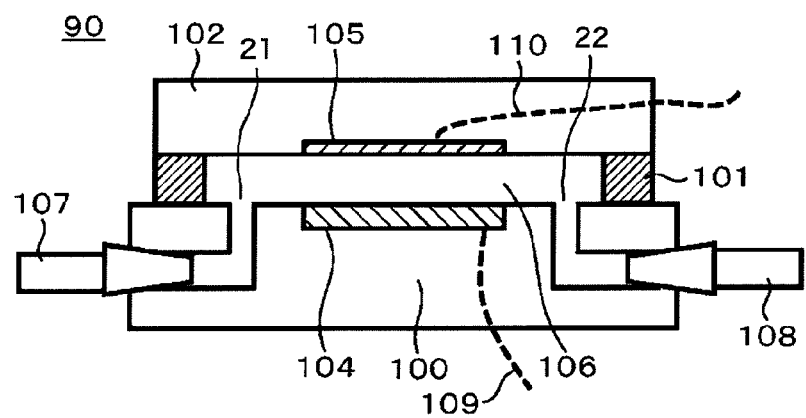
FIG. 13B is a cross-sectional assembly diagram of a further example of the flow cell used for an electrochemical analysis apparatus of an embodiment of the present invention.

FIG. 13A and FIG. 13B are diagrams showing a further example of the flow cell. In FIG. 13B, a flow cell 90 is formed by laminating respective members shown in FIG. 13A, that is, two electrically insulative substrates 100 and 102 and a seal member 101 in a manner shown in FIG. 13B. Secured to one surface of the insulative substrate 100 (the surface opposing the electrical insulative substrate 102) is a working electrode 104. A counter electrode 105 is fixed to one surface of the insulative substrate 102 (the surface opposing the electrical insulative substrate 100).

The working electrode 104 and the counter electrode 105 are connected by soldering to lead wires 109 and 110 before being embedded in the insulative substrates 100 and 102, respectively, and the lead wires 109, 110 are arranged to run through holes made in the insulative substrates 100, 102, respectively.

An opening 106 is formed at the center of the seal member 101. The shape of the opening 106 is a hexagon in the example shown in FIG. 13A although not specifically limited thereto as far as smooth liquid substitution is achievable without retention of each kind of solutions to be provided into the flow cell.

In the insulative substrate 100, holes 21 and 22 for coupling with pipes 107 and 108 are formed with the working electrode 104 being located therebetween; these two holes 21 and 22 are disposed to position them within the opening 106, thereby making it possible to take a solution into and out of the opening 106. The working electrode 104 and the counter electrode 105 oppose each other via the opening 106 of the seal member 101.

At four corners of the insulative substrates 100, 102 and the seal member 101, screw holes 103 are formed, through which screws are put respectively to thereby cramp and fasten the insulative substrate 100, the seal member 101, and the insulative substrate 102 together, thereby forming the flow cell 90.

In the insulative substrate 100, pipes 107 and 108 made of fluororesin are fixed and connected to a side face thereof. One of the pipes 107 and 108 is coupled, as will be described later, to a mechanism for introducing a solution under measurement or the like into the flow cell 90; the other is used as a flow path for exhausting the measurement-completed solution.

Beside, a reference electrode (not shown in FIG. 13B) is disposed at a solution exhaust-side pipe section and used as a reference electrode when applying a potential to the working electrode.

Figure 14A:
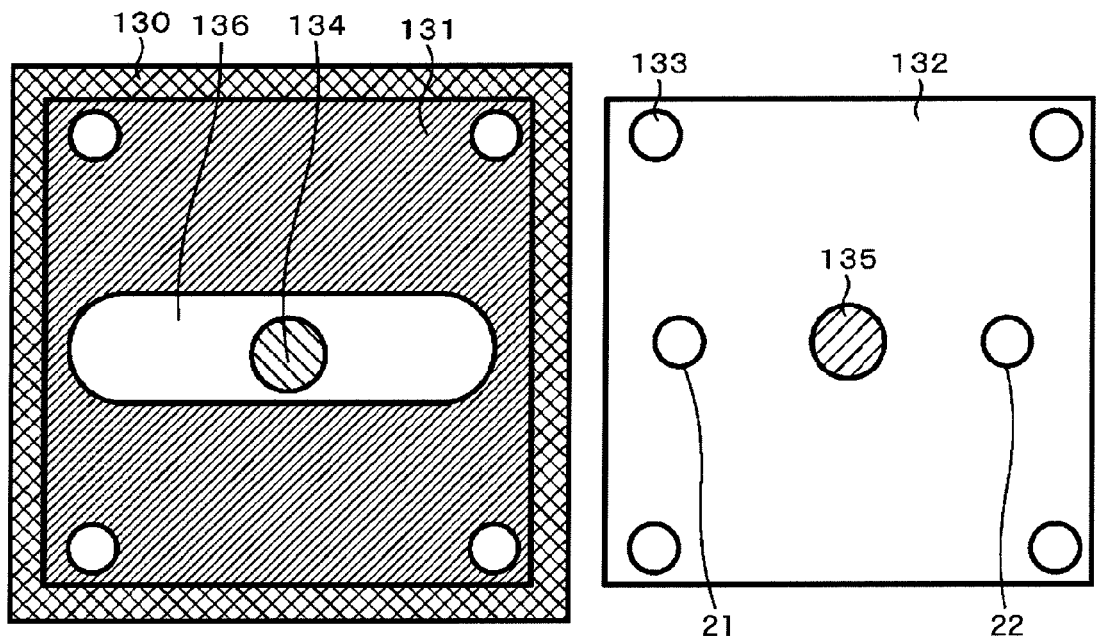
FIG. 14A is an exploded configuration diagram of another further example of the flow cell used for an electrochemical analysis apparatus of an embodiment of the present invention.
Figure 14B:
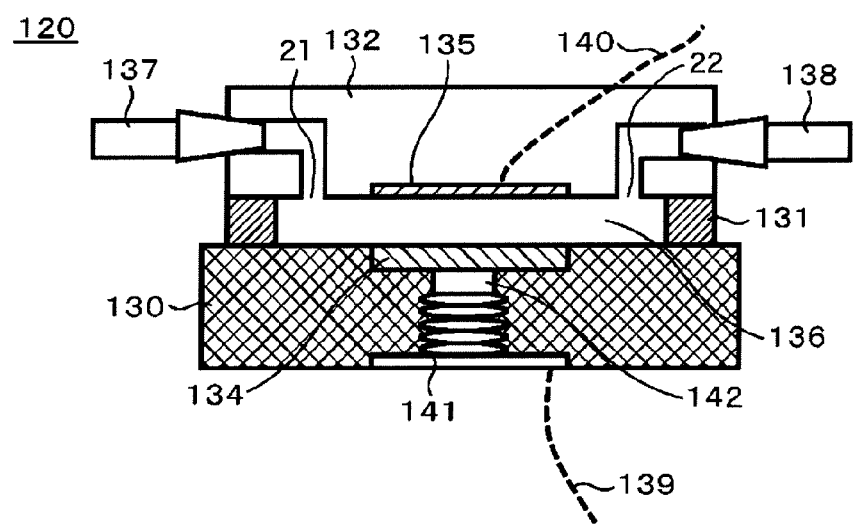
FIG. 14B is a cross-sectional assembly diagram of another further example of the flow cell used for an electrochemical analysis apparatus of an embodiment of the present invention.

FIG. 14A, FIG. 14B, and FIG. 14C are diagrams showing still another example of the flow cell. In FIG. 14B, a flow cell 120 is formed by laminating respective members shown in FIG. 14A, that is, two electrically insulative substrates 130 and 132 and a seal member 131 in a manner shown in FIG. 14B. Secured to one surface of the insulative substrate 132 (the surface opposing the electrical insulative substrate 130) is a counter electrode 135. At the center portion of the insulative substrate 130 a depression portion for disposing the working electrode 134 in a manner shown in FIG. 14C and a thread 143 for an electrically connecting bolt 141 for enabling connection with the working electrode 134.

After having the working electrode 134 adhere to the insulative substrate 130 using an adhesive, mechanical polishing is performed. Thereafter, the electrically connecting bolt 141 is screwed into the thread 143 via an electrically connecting plate 142. As long as the electrically connecting plate 142 is made of soft metals with low resistivity such as, for example, gold, tin, or aluminum, it is not specifically limited thereto. The electrically connecting bolt 141 is connected to a lead wire 139, thus enabling electrical connection with the working electrode 134.

The counter electrode 135 is connected by soldering to a lead wire 140 prior to being embedded in the insulative substrate 132 and the lead wire 140 is arranged to run through a hole made in the insulative substrate 132.

At the center of the seal member 131, an opening 136 is formed. In the insulative substrate 132, holes 21 and 22 for coupling with pipes 137 and 138 are formed while letting the counter electrode 135 lie therebetween; these two holes 21 and 22 are disposed to position them within the opening 136, thus making it possible to take a solution into and out of the opening 136. The working electrode 134 and the counter electrode 135 oppose each other via the opening 136 of the seal member 131.

At four corners of the insulative substrates 130, 132 and the seal member 131, screw holes 133 are formed, through which screws are put respectively to thereby cramp and fasten the insulative substrate 130, the seal member 131, and the insulative substrate 132 together, thereby forming the flow cell 120.

In the insulative substrate 132, pipes 137 and 138 made of fluororesin are fixed and connected to a side face of the surface on which the counter electrode 135 is placed. One of the pipes 137 and 138 is coupled, as will be stated later, to a mechanism for introducing a solution under measurement or the like into the flow cell 120; the other is for use as a flow path for exhausting the measurement-completed solution. Besides, a reference electrode (not shown in FIG. 14B) is placed at a solution exhaust-side pipe section and used as a reference electrode at the time of applying a potential to the working electrode 134.

FIG. 15 is a diagram showing still another further example of the flow cell. In FIG. 15, a flow cell 180 is formed by holding a working electrode 194 by and between an insulative substrate 190 and an insulative chassis 192 via O-rings 191. A plurality of screw holes 193 are formed at the outer periphery of the insulative substrate 190 and the insulative chassis 192; by running screws through the respective screw holes 193 and securing, the insulative substrates 190 and 192 are clamped together to thereby form the flow cell 180.

A counter electrode 195 is embedded at the center of the insulative chassis 192, providing a structure with the counter electrode 195 projecting toward the inside of the flow cell 180. Pipes 197 and 198 made of fluororesin are fixed and connected to the insulative chassis 192. One of the pipes 197 and 198 is coupled, as will be stated later, to a mechanism for introducing a solution under measurement or the like into the flow cell 180; the other is for use as a flow path for exhausting the measurement-completed solution. Besides, a reference electrode (not shown in FIG. 15) is disposed at a solution exhaust-side pipe section and used as a reference electrode in the event of applying a potential to the working electrode.

The working electrode 194 and the counter electrode 195 are connected by soldering to lead wires 199 and 200, respectively.

Next, an overall configuration of the electrochemical analyzer of Embodiment 3 of the present invention will be explained with reference to FIG. 10. For components similar to those of FIG. 1, detailed explanations are eliminated herein for purposes of avoiding redundancy.

In FIG. 10, a solution to be measured in the measurement solution vessel 8 and a buffer fluid in the buffer fluid vessel 9 are sucked by the solution-dispensing mechanism 11, mixed together in the solution inlet pipe 13, and then injected into the flow cell 20. While the mixed liquid is stored in the flow cell 20, a prescribed potential is applied by the voltage-applying means 5 to the working electrode 34 within the flow cell 20, thereby performing electrochemical measurement of the object to be assayed. A signal obtained by electrochemical reaction at the working electrode 34 within the flow cell 20 is transmitted via the lead wire 7 to the measuring means 6 for signal processing.

Incidentally, it is also possible to optically measure a change generated be an electrochemical reaction by disposing a detector above the substrate 32 made of transparent insulative resin.

The measurement-completed solution in the flow cell 20 is sucked by the solution exhaust mechanism 15 and then discarded to the waste container 16 through the solution outlet pipe 14.

The working electrode 34 used in Embodiment 3 is an electrode made of a composite material with zirconium oxide dispersed in platinum provided with electrical wiring. As a result of performing X-ray diffraction measurement of the electrode surface, it was revealed that the plane index (220) is preferentially oriented with its orientation ratio of 85%.

Using the flow cell of FIG. 11 and the electrochemical analyzer of FIG. 10, measurement was performed by a method of analyzing as the measurement solution a compound with TSH in blood serum being adsorbed to surfaces of magnetic particles with a diameter of 3 μm, and introducing, for example, potassium hydroxide aqueous solution as a cleaning fluid into the flow cell upon completion of each measurement. The variation range of the first and the 60,000th analyses was calculated in a similar way to Embodiment 1 to be 5.0%. In the flow cell and the analyzer using this electrode as its working electrode, the etching rate difference within the electrode surface is small so that advantageous effects were ascertained that non-uniform in-plane dissolution is suppressed and the crystal orientation property of crystals exposed to the top surface is small in change even when the analysis is repeated so that it becomes possible to reduce variations of the surface state and a fluctuation in the electrochemical response is small for a long time period, thus making it possible to obtain stable measurement results. It was also found that it becomes possible to stably perform liquid substitution of an analyte liquid and a cleaning fluid, thereby a variation in the electrochemical response being made small for a long time and enabling to obtain stable measurement results. It was further found that pits produced in the surface stabilize magnetic particles of the electrode surface so that stable measurement results are obtainable.

Embodiment 4

Embodiment 4 of the present invention will be explained. In Embodiment 4, iterative measurement was performed in a similar way to Embodiment 1 except that glucose of a known concentration was used as the analyte, enzyme was immobilized on the electrode surface of Embodiment 1, and the metal oxide dispersed in platinum was niobium oxide. The content of the metal oxide dispersed in platinum was 0.06% in the metal-equivalent value.

As a result of measurement, as shown in FIG. 17, it was found that the obtained variation range between the first and the 60,000th analyses was 4.0%, which is less than that of Comparative Example 2. This ascertained advantageous effects that in the analyzer using the present electrode as its working electrode, the etching rate difference within the electrode surface is small so that non-uniform in-plane dissolution is suppressed, and the crystal orientation property of crystals exposed to the top surface is small in change even when the analysis is repeated, thereby it becomes possible to suppress surface state variations, resulting in achievement of an ability to stably control the amount of enzyme modifying on the electrode surface, and it becomes possible to stably perform liquid substitution of an analyte liquid and a cleaning fluid, thereby a variation in the electrochemical response being made small for a long time period and enabling to obtain stable measurement results.

Embodiment 5

Embodiment 5 of the present invention will be explained. In Embodiment 5, iterative analytical measurement was performed pursuant to the measurement method of Embodiment 1 except that urea of a known concentration was used as the analyte and that the metal oxide dispersed in platinum was tantalum oxide. The content of the metal oxide dispersed in platinum was 0.08% in the metal-equivalent value. In the measurement solution vessel 8, an analyte sample was caused to be acted on with urease, next with β-nicotinamide adenine dinucleotide (NADH), and then with glutamate dehydrogenase in the presence of potassium ferricyanide, thereby producing potassium ferrocyanide. A solution under measurement containing potassium ferrocyanide from the measurement solution vessel 8 and a buffer fluid from the buffer fluid vessel 9 were introduced into the solution inlet pipe 13 to be mixed together and injected into the electrolysis cell 1 by the solution injection mechanism 12 so that electrochemical measurement was performed. As a result of execution of the iterative measurement, as shown in FIG. 17, it was found that the obtained variation range between the first and the 60,000th analyses was 2.5%, which is less than that of Comparative Example 3. This ascertained advantageous effects that in the analyzer using the present electrode as its working electrode, etching rate difference within the electrode surface is small so that non-uniform in-plane dissolution is suppressed, and the crystal orientation property of crystals exposed to the top surface is small in change even when the analysis is repeated, thereby it becomes possible to suppress surface state variations, and it becomes possible to stably perform liquid substitution of an analyte liquid and a cleaning fluid, thereby a variation in the electrochemical response being made small for a long time, and enabling to obtain stable measurement results.

Embodiment 6

Embodiment 6 of the present invention will be explained. In Embodiment 6, iterative analytical measurement was performed pursuant to the measurement method of Embodiment 5 except that cholesterol of a known concentration was used as the analyte, that the base metal was an alloy of platinum and 2% gold, and that the metal oxide dispersed in the base material was zirconium oxide. The content of the metal oxide dispersed in the base material was 0.1% in the metal-equivalent value. In the measurement solution vessel 8, an analyte sample was caused to be acted on with cholesterol oxidase, thereby producing hydrogen peroxide. A solution under measurement containing hydrogen peroxide from the measurement solution vessel 8 and a buffer fluid from the buffer fluid vessel 9 were introduced into the solution inlet pipe 13 to be mixed together and injected into the electrolysis cell 1 by the solution injection mechanism 12 so that electrochemical measurement was done. As a result of repeated execution of the measurement, as shown in FIG. 17, it was found that the obtained variation range between the first and the 60,000th analyses was 5.0%, which is less than that of Comparative Example 4. This ascertained advantageous effects that in the analyzer using the present electrode as its working electrode, etching rate difference within the electrode surface is small so that non-uniform in-plane dissolution is suppressed, and the crystal orientation property of crystals exposed to the top surface is small in change even when the analysis is repeated, thereby it becomes possible to suppress surface state variations, and it becomes possible to stably perform liquid substitution of an analyte liquid and a cleaning fluid, thereby a variation in the electrochemical reaction being made small for a long time, and enabling to obtain stable measurement results.

Embodiment 7

Embodiment 7 of the present invention will be explained. In Embodiment 7, iterative analytical measurement was performed pursuant to the measurement method of Embodiment 5 except that uric acid of a known concentration was used as the analyte, that the base metal was an alloy of platinum and 1% rhodium, and that the metal oxide dispersed in the base material was zirconium oxide. The content of the metal oxide dispersed in the base material was 0.15% in the metal-equivalent value. In the measurement solution vessel 8, an analyte sample was caused to be acted on with uricase, thereby producing hydrogen peroxide. A solution under measurement containing hydrogen peroxide from the measurement solution vessel 8 and a buffer fluid from the buffer fluid vessel 9 were introduced into the solution inlet pipe 13 to be mixed together and injected into the electrolysis cell 1 by the solution injection mechanism 12 so that electrochemical measurement was performed. As a result of repeated execution of the measurement, as shown in FIG. 17, it was found that the obtained variation range between the first and the 60,000th analyses was 5.3%, which is less than that of Comparative Example 5. This ascertained advantageous effects that in the analyzer using the present electrode as its working electrode, etching rate difference within the electrode surface is small so that non-uniform in-plane dissolution is suppressed, and the crystal orientation property of crystals exposed to the top surface is small in change even when the analysis is repeated, thereby it becomes possible to suppress surface state variations, and it becomes possible to stably perform liquid substitution of an analyte liquid and a cleaning fluid, thereby a variation in the electrochemical reaction being made small over a long time, and enabling to obtain stable measurement results.

Embodiment 8

Embodiment 8 of the present invention will be explained. In Embodiment 8, iterative analytical measurement was performed pursuant to the measurement method of Embodiment 5 except that creatinine of a known concentration was used as the analyte and that the metal oxide dispersed in the base material was zirconium oxide. The content of the metal oxide dispersed in the base material was 0.9% in the metal-equivalent value. It should be noted here that, although an electrode with the content of the metal oxide dispersed in the base material in excess of 1% was produced by way of trial, the machinability became impaired during adjustment of the electrode shape and, in the present embodiment, the electrode was adjusted so that it becomes 1% or less. In the measurement solution vessel 8, an analyte sample was caused to be acted on with creatininase and sarcosine oxidase sequentially, thereby producing hydrogen peroxide. A solution under measurement containing hydrogen peroxide from the measurement solution vessel 8 and a buffer fluid from the buffer fluid vessel 9 were introduced into the solution inlet pipe 13 to be mixed together and injected into the electrolysis cell 1 by the solution injection mechanism 12 so that electrochemical measurement was performed. As a result of repeated execution of the measurement, as shown in FIG. 17, it was revealed that the obtained variation range between the first and the 60,000th analyses was 7.7%, which is less than that of Comparative Example 6. This ascertained advantageous effects that in the analyzer using the present electrode as its working electrode, etching rate difference within the electrode surface is small so that non-uniform in-plane dissolution is suppressed, and the crystal orientation property of crystals exposed to the top surface is small in change even when the analysis is repeated, thereby it becomes possible to suppress surface state variations, and it becomes possible to stably perform liquid substitution of an analyte liquid and a cleaning fluid, thereby a variation in the electrochemical reaction being made small over a long time and enabling to obtain stable measurement results.

Embodiment 9

Embodiment 9 of the present invention will be explained. In Embodiment 9, iterative analysis measurement was performed pursuant to the measurement method of Embodiment 8 except that the content of the metal oxide dispersed in the base material was 0.004% in the metal-equivalent value. As a result of repeated execution of the measurement, as shown in FIG. 17, it was revealed that the obtained variation range between the first and the 60,000th analyses was 12.3%, which is slightly less than that of Comparative Example 7 so that a certain effect was seen but there was no great difference. This is speculated to be due to the reasons that in the analyzer using the present electrode as its working electrode, the content of the metal oxide in the base material is too small so that miniaturization of the crystalline texture of the base material did not progress appreciably and the crystal orientation ratio is less than that of Embodiment 8.

Embodiment 10

Embodiment 10 of the present invention will be explained. In Embodiment 10, iterative analytical measurement was done pursuant to the measurement method of Embodiment 3 except that fatty acid of a known concentration was used as the analyte. More specifically, an analyte sample was caused to be acted on with acyl-CoA-oxidase in the measurement solution vessel 8, thereby producing hydrogen peroxide. A solution under measurement containing hydrogen peroxide from the measurement solution vessel 8 and a buffer fluid from the buffer fluid vessel 9 were introduced into the solution inlet pipe 13 to be mixed together and injected into the flow cell 20 by a solution suction mechanism 15, so that electrochemical measurement was performed. As a result of repeated execution of the measurement, as shown in FIG. 17, it was found that the obtained variation range between the first and the 60,000th analyses was 5.1%, which is less than that of Comparative Example 8. This ascertained advantageous effects that in the analyzer using the present electrode as its working electrode, etching rate difference within the electrode surface is small so that non-uniform in-plane dissolution is suppressed, and the crystal orientation property of crystals exposed to the top surface is small in change even when the analysis is repeated, thereby it becomes possible to suppress surface state variations, and it becomes possible to stably perform liquid substitution of an analyte liquid and a cleaning fluid, thereby a variation in the electrochemical reaction being made small over a long time, and enabling to obtain stable measurement results.

Embodiment 11

Embodiment 11 of the present invention will be explained. In Embodiment 11, iterative analytical measurement was done pursuant to the measurement method of Embodiment 3 except that bilirubin of a known concentration was used as the analyte. More specifically, an analyte sample was caused to be acted on with bilirubin oxidase in the presence of potassium ferricyanide, thereby producing potassium ferrocyanide. A solution under measurement containing potassium ferrocyanide from the measurement solution vessel 8 and a buffer fluid from the buffer fluid vessel 9 were introduced into the solution inlet pipe 13 to be mixed together and injected into the flow cell 20 by the solution suction mechanism 15, so that electrochemical measurement was performed. As a result of repeated execution of the measurement, as shown in FIG. 17, it was found that the obtained variation range between the first and the 60,000th analyses was 5.3%, which is less than that of Comparative Example 9. This ascertained advantageous effects that in the analyzer using the present electrode as its working electrode, etching rate difference within the electrode surface is small so that non-uniform in-plane dissolution is suppressed, and the crystal orientation property of crystals exposed to the top surface is small in change even when the analysis is repeated, thereby it becomes possible to suppress surface state variations, and it becomes also possible to stably perform liquid substitution of an analyte liquid and a cleaning fluid, thereby a variation in the electrochemical reaction being made small over a long time, and enabling to obtain stable measurement results.

Embodiment 12

In Embodiment 12, an electrode was fabricated with a metal base made of titanium and its surface platinum plated and a film formed by applying zirconium oxide and being sintered. A detailed explanation of the fabrication method will be given below. After having degreased and rinsed a titanium plate of 10 mm×10 mm and 0.5 mm in thickness, it was treated with a 5% hydrofluoric acid aqueous solution for 2 minutes. After rinsing with water, plating was performed for 1 minute in a sulfuric acid aqueous solution containing diamminedinitritoplatinum at 15 mA/cm². Next, heating was done at 400° C. in the air for 1 hour. Next, after a butanol solution of chloroplatinic acid (10 g/L in platinum metal equivalent) and an ethanol solution of zirconium chloride (1 g/L in zirconium metal equivalent) are mixed together by the equal amount to prepare a coating liquid, this coating liquid was used to measure 3 μL per 1 cm², and applied to a platinum-plated titanium base substance. Thereafter, it was vacuum-dried at room temperature for 30 minutes and further sintered in the air at 500° C. for 10 minutes. This process was repeated fifty times whereby a zirconium oxide-dispersed platinum electrode was obtained. The metal oxide content ratio of this electrode was 9.7%. As a result of X-ray diffraction measurement of the electrode surface, the preferential orientation ratio was 47%. Using the electrochemical analyzer of FIG. 1 which uses the aforementioned electrode as its working electrode, measurement was performed in a similar manner to Embodiment 1 by a method for immunologically analyzing as the measurement solution a TSH in blood serum and for introducing, for example, potassium hydroxide aqueous solution as a cleaning liquid into the electrolysis cell at each measurement completion. A measurement result revealed that the obtained variation range between the first and the 60,000th analyses was 8.7% as shown in FIG. 17.

Embodiment 13

In Embodiment 13, iterative analytical measurement was performed in a similar way to Embodiment 12 except that the zirconium oxide was replaced with a niobium oxide. As a result of the measurement, it was found that the obtained variation range between the first and the 60,000th analyses was 9.4% as shown in FIG. 17.

Embodiment 14

In Embodiment 14, analysis measurement was repeatedly performed in a similar way to Embodiment 12 except that the zirconium oxide was replaced by a tantalum oxide. As a result of the measurement, it was found that the obtained variation range between the first and the 60,000th analyses was 9.2% as shown in FIG. 17.

In the case of using the electrodes of Embodiments 12 to 14, there was an effect on reduction of the variation range when compared with Comparative Example 1; however, such effect was smaller than that of Embodiment 1. It is considered that this is because the electrodes of Embodiments 12 to 14 are those fabricated by applying and sintering processes and are larger than Embodiment 1 in concentration of the metal oxide contained in the base material and smaller in the crystal orientation ratio. Namely, it is perceived that the etching rate difference within the electrode surface becomes greater as the surface etching progresses to allow a specific plane to dissolve preferentially whereby large step-like differences were locally generated in the electrode surface. In addition, a phenomenon was also observed of dropping of the electrode material with the progress of surface etching since it is the zirconium oxide-dispersed platinum electrode fabricated by applying and sintering processes so that it is lower in the film strength compared with the rolled electrode of Embodiment 1. Furthermore, it is also conceivable that the largeness of metal oxide concentration affected the electrochemical reaction. As a result, it can be considered that the variation of the electrode surface state becomes large so that stable implementation of liquid substitution of an analyte liquid and a cleaning fluid becomes unable, thus causing the variation of electrochemical response to increase in a long-term view.

Embodiment 15

Next, Embodiment 15 of the present invention will be explained. This Embodiment 15 is similar to Embodiment 1 except that the working electrode 2 was fabricated by integrally laminating the platinum and the valve metal.

Here, the working electrode 2 was produced by a working electrode manufacturing apparatus 52 shown in FIG. 18 in a procedure described below.

Figure 18:
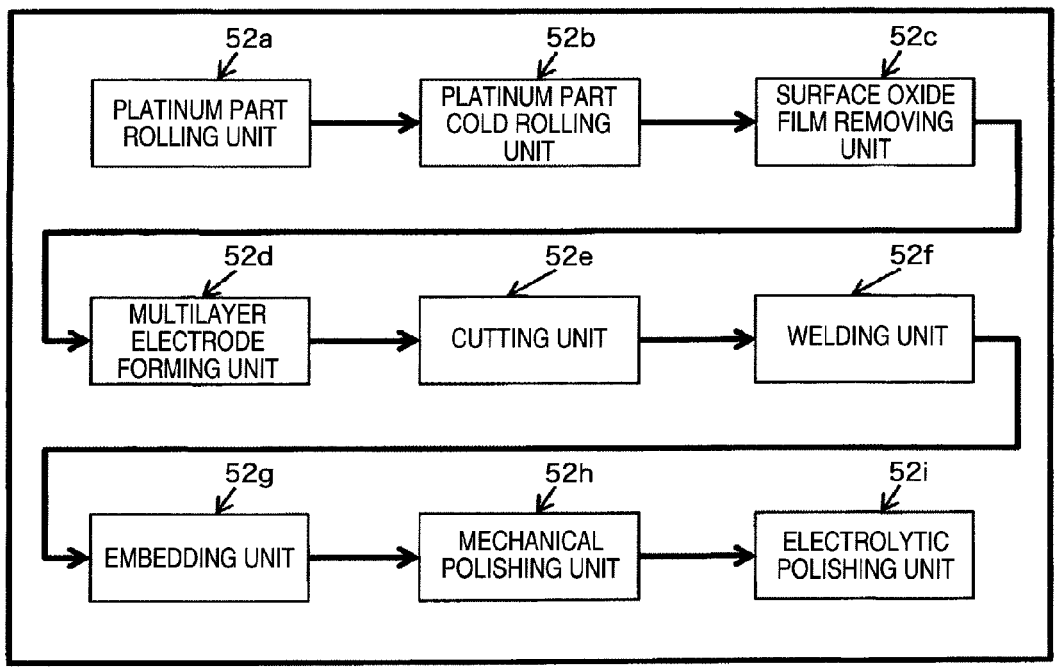
FIG. 18 is a schematic configuration diagram of a manufacturing apparatus of an electrode for electrochemical measurement in accordance with one embodiment of the present invention.

In FIG. 18, the platinum is pressed by a platinum plate machining unit 52a at 30 MPa in a nitrogen atmosphere. Then, at the platinum machining unit 52a, the platinum plate is heated up to 800 degrees for 1 hour and subjected to hot rolling at 100 MPa, thereby fabricating a platinum plate of 5 mm in thickness. Subsequently, at a platinum plate cold rolling unit 52b, the platinum plate that was machined in the rolling unit 52a is cold rolled at 100 MPa, thereby forming a platinum plate with a thickness of 1 mm. Thereafter, at a surface oxide film removing unit 52c, the platinum plate that was processed in the platinum plate cold rolling unit 52b and a titanium plate of 0.5 mm in thickness are introduced into a vacuum chamber for performing dry etching of the titanium plate surface to thereby remove the surface oxide layer. Thereafter, by a multilayer electrode forming unit 52d, the platinum plate and the titanium plate are rapidly laminated together and cold rolled in a vacuum at 450 degrees in such a manner that the film thickness of the platinum plate becomes 100 μm, thereby obtaining a multilayer electrode of platinum/titanium having at its platinum part a layered crystal texture with a thickness of 5 μm or less.

Next, the multilayer electrode that was formed by the multilayer electrode forming unit 52d is cut at a cutting unit 52e into a size of 5 mm×15 mm. Thereafter, the cut multilayer electrode is at an electroding unit 52f bent with its end portion by 90 degrees and the platinum surface and a conductive wire are connected together by soldering.

Next, at a resin embedding unit 52g, it is buried in a fluorine-based resin using an adhesive agent in such a manner that only the platinum surface of the multilayer electrode is exposed by its area of 5 mm×10 mm.

Subsequently, at a mechanical polishing unit 52h, the platinum surface is mechanically polished using water-proof abrasive paper, diamond paste, and alumina particles sequentially, thus obtaining a mirror finished plane.

Finally, at an electrolytic polishing unit 52i, electrical potential scanning between potential levels of −1.2 to 1.0V vs. Ag|AgCl is repeated 10,000 times at a potential scanning rate of 0.1 V/s in a 0.2 mol/L potassium hydroxide aqueous solution, thereby obtaining the working electrode 2.

X-ray diffraction measurement was performed of the electrode surface of the working electrode 2 used in this Embodiment 15. CuKα was used as an X-ray source to measure three different points on the platinum surface with output settings of 40 kV and 20 mA. Integration values (I) of diffraction peaks of a (111) plane, a (200) plane, a (220) plane, and a (311) plane on the platinum surface were calculated to thereby obtain each direction's orientation ratio ((%)=I(hkl)/ΣI(hkl)×100). Incidentally, the calculation of each peak integration value was done in ranges of 37°≤2θ≤42° for the (111) plane, 44°≤2θ≤49° for the (200) plane, 65°≤2θ≤70° for the (220) plane, 78°≤2θ≤83° for the (311) plane, respectively (where θ is the diffraction angle). As results of the measurement, it was revealed that the plane index (220) if preferentially oriented with its orientation ratio of 97% as in the result of Embodiment 15 shown in FIG. 19.

The through-thickness cross-section of a similarly produced multilayer electrode was exposed and its platinum part was analyzed by means of an electron beam backscatter pattern. Analysis results are shown in FIG. 20A and FIG. 20B.

Figure 20A:
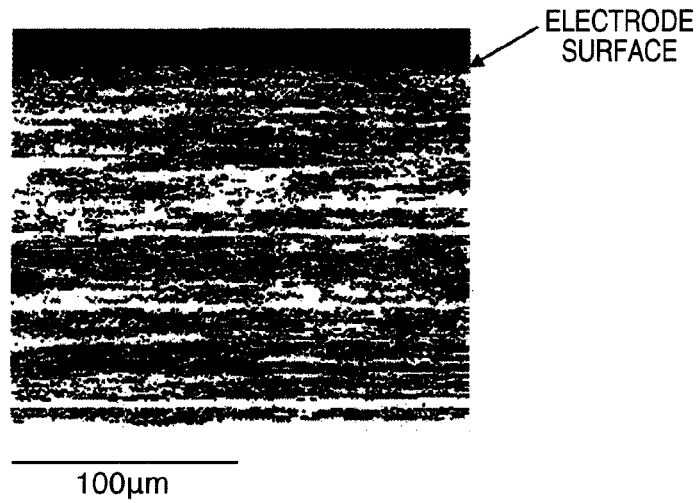
FIG. 20A is a diagram showing an analysis result of crystalline texture of a cross-section in the plate thickness direction of an electrode in accordance with one embodiment of the present invention.

As shown in FIG. 20A, it was found that the obtained working electrode has a layered crystal texture with respect to the electrode surface. To calculate the thickness of a platinum crystal layer, an area of 25 μm×25 μm was subjected to measurement of three fields of view while letting a region of 0.075 μm×0.075 μm be data of one point and the thickness of a layer having a maximal layer thickness in the measured surface was measured.

Figure 20B:
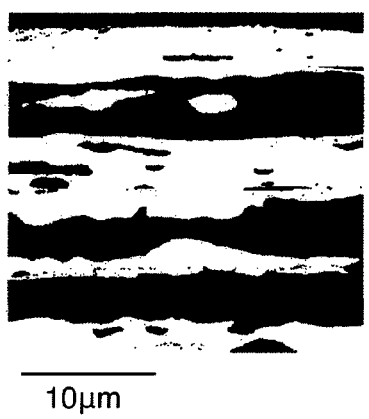
FIG. 20B is a magnified diagram showing a near-surface analysis result of crystal texture of a cross-section in the plate thickness direction of an electrode in accordance with one embodiment of the present invention.

A typical near-surface crystal texture image of the present electrode is shown in FIG. 20B. The layer thickness was found to be 5 μm or less at most.

Figure 21:
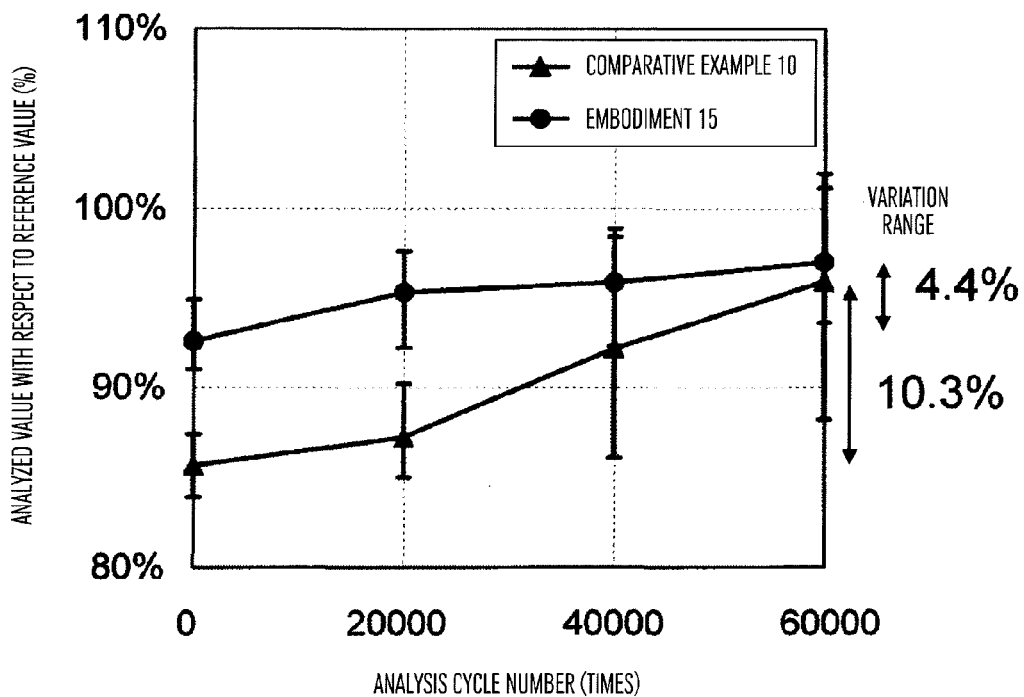
FIG. 21 is a diagram for explanation of effects of a platinum electrode based on one embodiment of the present invention.

FIG. 21 is a diagram for explanation of an effect of the platinum electrode employed in Embodiment 15 of the present invention. Note that the data shown in FIG. 21 is the date obtained by repeated execution of measurement with TSH (thyroid-stimulating hormone) of the same concentration as the analyte. The abscissa of FIG. 21 indicates the number of times of testing and the ordinate indicates a value of each measurement value divided by a reference value. Furthermore, the reference value is an output value upon measurement of a TSH-containing solution of a pre-determined concentration and the actual measurement value is a measured value obtained when measuring each of the solutions used in Embodiment 15 and Comparative Example 10. The variation range is defined to be a difference between values of the 60,000th and the first analyses.

In FIG. 21, lines connecting circles are in the case of Embodiment 15 of the present invention; lines connecting triangles are in the case of Comparative Example 10 different from the present invention.

By using the electrochemical analyzer of FIG. 1, measurement was performed by a method for immunologically analyzing as the measurement solution a chemical component contained in a liquid sample such as blood or urine—for example, TSH in blood serum—and introducing, for example, potassium hydroxide aqueous solution as a cleaning fluid into the electrolysis cell at every completion of each measurement.

As shown in FIG. 21, the variation range in the case of using an electrode of the comparative example was 10.3%. The electrode of Comparative Example 10 is a multilayer electrode of platinum and titanium subjected to hot rolling and recrystallization treatments and is the electrode that underwent mechanical polishing and electrolytic treatment of the platinum surface in a similar way to Embodiment 15. Details will be explained in Comparative Examples described later. In contrast, in the case of using the platinum electrode of Embodiment 15 of the present invention, the variation range was reduced to 4.4%.

The electrode of Embodiment 15 of the present invention is the multilayer electrode in which the platinum part's cross-section crystal texture in the plate thickness direction is formed in the form of layers with respect to the electrode surface with a layer thickness being less than or equal to 5 μm. And, in the electrode in accordance with Embodiment 15 of this invention the surface alteration layer with a disordered crystal orientation property created in rolling and mechanical polishing processes was removed away and it is preferentially oriented in the plane direction (220) with its orientation ratio of 90% or higher. It was revealed that in the electrochemical analyzer using the electrode of Embodiment 15 of the present invention as its working electrode, since the etching rate difference within the electrode surface is small, the unevenness created due to etching is small and it becomes possible to suppress variations of the surface area so that the variation in the electrochemical response is small over a long time, thereby making it possible to obtain stable measurement results.

Embodiment 16

Next, Embodiment 16 of the present invention will be explained. An electrode of this Embodiment 16 and an electrochemical analyzer using it are similar to those of Embodiment 15 except that in the manufacture of the electrode the aforementioned electrode was immersed in a prescribed electrolytic solution during electrolytic polishing processing so that an alteration layer of the platinum surface was removed while diagnosing by cyclic voltammetry the surface state.

Figure 22:
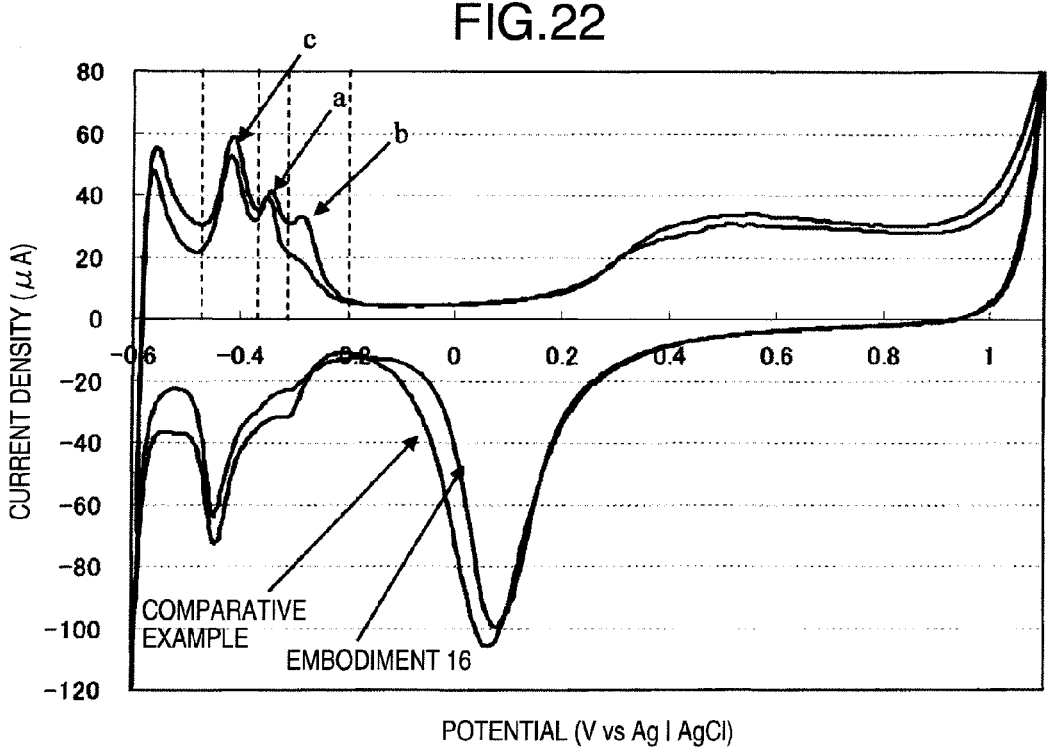
FIG. 22 is a cyclic voltammogram of electrodes of one embodiment of the present invention and that of a comparative example.

The cyclic voltammetry was conducted under conditions of using a nitrogen-substituted phosphoric acid buffer solution of a pH of 6.86 as the electrolytic solution, a platinum wire as the working electrode, Ag|AgCl as the reference electrode, the potential scanning range of −0.6 to 1.1 V, and the scanning rate of 0.1 V/s. A measurement result is shown in FIG. 22. For comparison purposes, a result of Comparative Example 10 is shown together.

Among a plurality of hydrogen absorption/desorption current peaks obtained from the result of cyclic voltammetry, letting "a" be a peak observed in a range of −0.37 to −0.31 V and "b" be a peak seen in a range of −0.31 to −0.2 V, their peak areas and an area ratio b/a are calculated. Electrolytic treatment was performed until the area ratio becomes 80% or less; thus, the working electrode 2 was obtained.

As a result of iterative analysis by the electrochemical analyzer using the working electrode in accordance with Embodiment 16 of the present invention in a similar way to Embodiment 15, an excellent result of the variation range of 4.2% was obtained. As a result of X-ray diffraction analysis of an electrode which was fabricated in a similar way and is different from the present invention, it was observed to be preferential oriented in the (220) direction with an orientation ratio of 98%. In the electron beam backscatter pattern analysis also, the thickness of a crystal texture layer of platinum plate-thickness cross-section was 5 µm or less. In an analyzer using as its working electrode the electrode in accordance with Embodiment 16 of this invention, since the etching rate difference within the electrode surface is small, the unevenness created due to etching is small and it becomes possible to suppress variations of the surface area so that the variation in the electrochemical response is small over a long time, thereby making it possible to obtain stable measurement results.

Although in Embodiment 16 of this invention the peaks a and b are used as the criterion for judgment of degree of the surface alteration layer removal, it was ascertained that similar results are also obtainable by calculating a ratio b/c from the peak c seen in the range of −0.48 to −0.37 V and the peak b and for letting b/c be 35% or less as the criterion.

Embodiment 17

An electrochemical analysis apparatus in accordance with Embodiment 17 of the present invention is similar to the electrochemical analyzer of Embodiment 2 except for the manufacturing method of the working electrode 34.

Here, in FIG. 11, a flow cell 20 serving as an electrolysis cell is formed by laminating two electrically insulative substrates 30 and 32 and a sealing member 31 shown in FIG. 11A in a way shown in FIG. 11B. The insulative substrate 30 is made of polyether ether ketone. The material of this insulative substrate 30 is not specifically limited thereto as far as it is an insulative resin excellent in chemical resistance; fluorine-based resin, polystyrene, polyethylene, polypropylene, polyester, polyvinyl chloride, epoxy resin, polyimide, polyamide-imide, polysulfone, polyether sulfone, polyphenylene sulfide, acrylic resin, and the like may be used.

On one surface of the insulative substrate 30 (the surface opposing the electrically insulative substrate 32), a working electrode 34 is fixed. A manufacturing method of the working electrode 34 will be shown below.

Namely, those processes prior to the mechanical polishing of Embodiment 15 of the present invention were performed to obtain a platinum/titanium multilayer electrode. This multilayer electrode was embedded in a depression portion provided in the surface of the insulative substrate 30 and, after bonded by an adhesive agent, mechanical polishing was applied thereto using water-proof abrasive paper, diamond paste, and alumina particles sequentially until a step-like surface difference between the insulative substrate 30 and the multilayer electrode disappeared, thereby obtaining a mirror-finished surface. Incidentally, as for the adhesive agent a resin material with thermoplasticity, thermalsetting, or photohardening such as an epoxy-based or acrylic substance may be used; it is not specifically limited thereto and may be properly chosen as long as it is excellent in chemical resistance similar to the insulative resin. [0063] Thereafter, application of electrical potential having rectangular pulses of −1.2 V/0.5 sec and 3.0 V/1.5 sec was repeated 10,000 times in 0.2 mol/L potassium hydroxide aqueous solution.

In Embodiment 17 of the present invention, the working electrode 4 was placed so that the rolling direction is perpendicular to the direction along which a liquid flows during analysis.

As a result of X-ray diffraction measurement of the electrode surface of the working electrode 34 used in this Embodiment 17 it was revealed that the plane index (220) was preferentially oriented with its orientation ratio is 92%. It was also revealed by electron beam backscatter pattern analysis that the working electrode 34 has a laminar crystal texture with respect to the electrode surface and that the layer thickness of platinum is 5 µm or less at most.

By using the electrochemical analyzer shown in FIG. 10, measurement was done by a method for analyzing as the measurement solution a chemical component contained in a liquid sample such as blood or urine—for example, a compound with TSH in blood serum being adsorbed in the surface of a magnetic bead(s) with a diameter of 3 µm—and introducing as a cleaning fluid, for example, potassium hydroxide aqueous solution into the electrolysis cell at every completion of each measurement.

The variation range between the first and the 60,000th analyses was obtained in a similar way to Embodiment 15 to be 5.1%. In the analyzer using the electrode of Embodiment 17 of the present invention as its working electrode, since the etching rate difference within the electrode surface is small, the unevenness created due to etching is small and it becomes possible to suppress variations of the surface area. It was ascertained that it becomes also possible to stably perform liquid substitution of an analyte liquid and a cleaning fluid so that the variation in the electrochemical response is small for a long time period, thereby enabling stable measurement results to be obtained.

In addition, another effect was recognized that the beads are prevented from flowing downstream from the working electrode by disposing the working electrode such that its rolling direction is perpendicular to the flow direction of the analyte liquid, thereby making it possible to obtain stable measurement results with small variations over a long time.

Incidentally, in this Embodiment 17 the working electrode 34 is placed so that its rolling direction is perpendicular to the direction of the analyte liquid flowing; however, the case of setting the rolling direction to the same direction as the flow direction was investigated ant the results revealed that the variation range was 7%, which is slightly greater than that of the present Embodiment 17. The data stability within a short period of time was also evaluated to reveal that data variability becomes larger when compared to this embodiment. This is considered to be due to the influence of slight downstream outflow of the magnetic beads from the working electrode surface during analysis.

Thus, it was found that, as shown in this Embodiment 17, it is a more preferable form for improvement of the data stability to place the working electrode 34 so that the rolling direction is perpendicular to the analyte liquid's flow direction during analysis.

Embodiment 18

Next, Embodiment 18 of the present invention will be explained. In Embodiment 18, enzyme is immobilized on the surface of the electrode of Embodiment 15, with an underlayer metal being made of Nb. The other arrangements are similar to those of Embodiment 15. In Embodiment 18, iterative measurement was performed in a similar way to Embodiment 15 while letting glucose of a known concentration be the analyte.

As a result of measurement, as shown in FIG. 24, it was found that the variation range between the first and the 60,000th analyses was 4.1%, which is less than that of Comparative Example 11 with glucose as its analyte. This is because, in the analyzer using the electrode of Embodiment 18 of the present invention as its working electrode, since the etching rate difference within the electrode surface is small, the unevenness created due to etching is small, and it becomes possible to suppress variations of the surface area, resulting in achievement of an ability to stably control the amount of enzyme modifying on the electrode surface. In addition, it is ascertained that according to Embodiment 18 of this invention it becomes possible to stably perform liquid substitution of an analyte liquid and a cleaning fluid so that the variation in the electrochemical response is small over a long time, thereby making it possible to obtain stable measurement results.

As for Comparative Example 11 shown in FIG. 24, its explanation will be given later.

Embodiment 19

Next, Embodiment 19 of the present invention will be explained. In Embodiment 19, iterative analytical measurement was performed pursuant to the measurement method of Embodiment 15 except that urea of a known concentration was taken as the analyte. Namely, in the measurement solution vessel 8, an analyte sample was caused to be acted on with urease, next with β-nicotinamide adenine dinucleotide (NADH), and further with glutamate dehydrogenase in the presence of potassium ferricyanide, thereby producing a potassium ferrocyanide.

A solution under measurement containing potassium ferrocyanide from the measurement solution vessel 8 and a buffer fluid from the buffer fluid vessel 9 were introduced into the solution inlet pipe 13 to be mixed together and then injected into the electrolysis cell 1 by the solution injection mechanism 12 so that electrochemical measurement was done. As a result of repeated execution of such measurement, as shown in FIG. 24, it was found that the obtained variation range between the first and the 60,000th analyses was 2.8%, which is less than that of Comparative Example 12 using the same analyte.

This is because in the analyzer using this electrode as its working electrode, since the etching rate difference within the electrode surface is small, the unevenness created due to etching is small and it is possible to suppress variations of the surface area.

Additionally, it is ascertained that according to Embodiment 19 of the present invention it becomes possible to stably perform liquid substitution of an analyte liquid and a cleaning fluid so that the variation in the electrochemical response is small over a long time, thus making it possible to obtain stable measurement results.

Embodiment 20

Next, Embodiment 20 of the present invention will be explained. Embodiment 20 is such that the underlayer metal is Zr. The other arrangements are similar to those of Embodiment 15. In Embodiment 20, cholesterol of a known concentration was taken as the analyte, and iterative analytic measurement was performed pursuant to the measurement method of Embodiment 15.

Namely, in the measurement solution vessel 8 of FIG. 1, an analyte sample was caused to be acted on with cholesterol oxidase to produce hydrogen peroxide. Then, a measurement solution containing hydrogen peroxide from the measurement solution vessel 8 and a buffer fluid from the buffer fluid vessel 9 were introduced into the solution inlet pipe 13 to be mixed together and then injected into the electrolysis cell 1 by the solution injection mechanism 12 so that electrochemical measurement was performed.

As a result of repeated execution of the measurement, as shown in FIG. 24, the obtained variation range between the first and the 60,000th analyses was found to be 5.8%, which is less than that of Comparative Example 13 using the same analyte. This is because in the analyzer using this electrode as its working electrode, since the etching rate difference within the electrode surface is small, the unevenness created due to etching is small and it becomes possible to suppress variations of the surface area.

Additionally, it is ascertained that according to Embodiment 20 of the present invention it becomes possible to stably perform liquid substitution of an analyte liquid and a cleaning fluid so that the variation in the electrochemical response is small over a long time, thus making it possible to obtain stable measurement results.

Embodiment 21

Next, Embodiment 21 of the present invention will be explained. In Embodiment 21, analytical measurement was repeatedly performed pursuant to the measurement method of Embodiment 15 except that in Embodiment 21 taken as its analyte uric acid of a known concentration.

Namely, in the measurement solution vessel 8, an analyte sample was caused to be acted on with uricase to produce hydrogen peroxide. A measurement solution containing hydrogen peroxide from the measurement solution vessel 8 and a buffer fluid from the buffer fluid vessel 9 were introduced into the solution inlet pipe 13 to be mixed together and then injected into the electrolysis cell 1 by the solution injection mechanism 12 so that electrochemical measurement was done.

As a result of repeated execution of the measurement, as shown in FIG. 24, the obtained variation range between the first and the 60,000th analyses was found to be 6.5%, which is less than that of Comparative Example 14 using the same analyte. This is because in the analyzer using this electrode as its working electrode, since the etching rate difference within the electrode surface is small, the unevenness created due to etching is small and it becomes possible to suppress variations of the surface area.

Additionally, it is ascertained that according to Embodiment 21 of the present invention it becomes possible to stably perform liquid substitution of an analyte liquid and a cleaning fluid so that the variation in the electrochemical response is small over a long time, thereby making it possible to obtain stable measurement results.

Embodiment 22

Next, Embodiment 22 of the present invention will be explained. In Embodiment 22, analytical measurement was repeatedly performed pursuant to the measurement method of Embodiment 15 except that in Embodiment 22 creatinine of a known concentration is taken as its analyte.

Namely, in the measurement solution vessel 8, an analyte sample was caused to be acted on with creatininase and sarcosine oxidase sequentially to produce hydrogen peroxide. A measurement solution containing hydrogen peroxide from the measurement solution vessel 8 and a buffer fluid from the buffer fluid vessel 9 were introduced into the solution inlet pipe 13 to be mixed together and then injected into the electrolysis cell 1 by the solution injection mechanism 12 so that electrochemical measurement was performed.

As a result of repeated execution of the measurement, as shown in FIG. 24, the obtained variation range between the first and the 60,000th analyses was found to be 7.9%, which is less than that of Comparative Example 15 using the same analyte. This is because in the analyzer using this electrode as its working electrode, since the etching rate difference within the electrode surface is small, the unevenness created due to etching is small and it becomes possible to suppress variations of the surface area.

Additionally, it is ascertained that according to Embodiment 22 of the present invention it becomes possible to stably perform liquid substitution of an analyte liquid and a cleaning fluid so that the variation in the electrochemical response is small in variation over a long time, thus making it possible to obtain stable measurement results.

Embodiment 23

Next, Embodiment 23 of the present invention will be explained. In Embodiment 23, analytical measurement was repeatedly performed pursuant to the measurement method of Embodiment 15 except that in Embodiment 23 creatinine of a known concentration is taken as its analyte.

An analyte sample was caused to be acted on with creatininase and sarcosine oxidase sequentially to produce hydrogen peroxide. A solution under measurement containing hydrogen peroxide from the measurement solution vessel 8 and a buffer fluid from the buffer fluid vessel 9 were introduced into the solution inlet pipe 13 to be mixed together and then injected into the electrolysis cell 1 by the solution injection mechanism 12 so that electrochemical measurement was performed.

As a result of repeated execution of the measurement, as shown in FIG. 24, the obtained variation range between the first and the 60,000th analyses was found to be 9.8%, which is less than that of Comparative Example 16 using the same analyte. This is because in the analyzer using this electrode as its working electrode, since the etching rate difference within the electrode surface is small, the unevenness created due to etching is small and it becomes possible to suppress variations of the surface area.

Additionally, it is ascertained that according to Embodiment 23 of the present invention it becomes possible to stably perform liquid substitution of an analyte liquid and a cleaning fluid so that the variation in the electrochemical response is small over a long time, thus making it possible to obtain stable measurement results.

Embodiment 24

Next, Embodiment 24 of the present invention will be explained. In Embodiment 24, analytical measurement was repeatedly performed pursuant to the measurement method of Embodiment 15 except that in Embodiment 24 fatty acid of a known concentration is taken as the analyte.

Namely, in the measurement solution vessel 8, an analyte sample was caused to be acted on with acyl-CoA-oxidase to produce hydrogen peroxide. A solution under measurement containing hydrogen peroxide from the measurement solution vessel 8 and a buffer fluid from the buffer fluid vessel 9 were introduced into the solution inlet pipe 13 to be mixed together and then injected into the electrolysis cell 1 by the solution injection mechanism 12 so that electrochemical measurement was performed.

As a result of repeated execution of the measurement, as shown in FIG. 24, the obtained variation range between the first and the 60,000th analyses was found to be 5.9%, which is less than that of Comparative Example 17 using the same analyte.

This is because in the analyzer using this electrode as its working electrode, since the etching rate difference within the electrode surface is small, the unevenness created due to etching is small and it becomes possible to suppress variations of the surface area.

Additionally, it is ascertained that according to Embodiment 24 of the present invention it becomes possible to stably perform liquid substitution of an analyte liquid and a cleaning fluid so that the variation in the electrochemical response is small over a long time, thus making it possible to obtain stable measurement results.

Embodiment 25

Next, Embodiment 25 of the present invention will be explained. In Embodiment 25, analytical measurement was repeatedly performed pursuant to the measurement method of Embodiment 15 except that in Embodiment 25 used bilirubin of a known concentration is taken as the analyte.

Namely, in the measurement solution vessel 8, an analyte sample was caused to be acted on with bilirubin oxidase in the presence of potassium ferricyanide to produce potassium ferrocyanide. A solution under measurement containing potassium ferrocyanide from the measurement solution vessel 8 and a buffer fluid from the buffer fluid vessel 9 were introduced into the solution inlet pipe 13 to be mixed together and then injected into the electrolysis cell 1 by the solution injection mechanism 12 so that electrochemical measurement was done.

As a result of repeated execution of the measurement, as shown in FIG. 24, the obtained variation range between the first and the 60,000th analyses was found to be 4.3%, which is less than that of Comparative Example 18 using the same analyte.

This is because in the analyzer using this electrode as its working electrode, since the etching rate difference within the electrode surface is small, the unevenness created due to etching is small and it becomes possible to suppress variations of the surface area.

Additionally, it is ascertained that according to Embodiment 25 of the present invention it becomes possible to stably perform liquid substitution of an analyte liquid and a cleaning fluid so that the variation in the electrochemical response is small over a long time, thus making it possible to obtain stable measurement results.

Comparative Example 1

A working electrode 2 of the comparative example is an electrode with platinum being rolled to a plate-like shape. It was heated up to 800° C. for 1 hour and hot rolled at 100 MPa so that its thickness becomes 0.1 mm. After cooling, it was embedded in fluorine-based resin, subjected to mechanical polishing by sequentially using water-proof abrasive paper, diamond paste, and alumina, and continuously subjected to electrolytic polishing, thereby obtaining the working electrode in a similar way to Embodiment 1.

Using this working electrode in the electrochemical analyzer of FIG. 1, measurement was performed, similar to Embodiment 1, by a method for immunologically analyzing as the measurement solution TSH in blood serum and introducing as a cleaning fluid, for example, potassium hydroxide aqueous solution into the electrolysis cell at every completion of each measurement.

As a result, as shown in FIG. 6, a variation range in the case of using the electrode of the comparative example was 10.3%. As the electrode of the comparative example was analyzed by X-ray diffraction, it was revealed to be preferentially oriented to (220) and (111) as shown in FIG. 5; however, the orientation ratio of the (220) direction exhibiting a maximal intensity was found to be 54%. In addition, observation of the crystalline texture of the cross-section in the plate thickness direction of the electrode of Comparative Example 1 revealed that it contains coarse crystal textures with large grain sizes. It is considered to be attributed to production of large step-like differences locally in the electrode plane by the etching rate difference within the electrode surface being large and a specific plane dissolving preferentially with repeated execution of analysis, that is, with the progress of surface etching in the case of using such an electrode. Also, the orientation ratios of respective crystalline directions exposed to the top surface change with repeated execution of analysis. As a result, it is considered that the variation of the electrode surface state becomes large and it becomes impossible to stably perform liquid substitution of an analyte liquid and a cleaning fluid, thereby causing the variation of the electrochemical response to become large when looking at on a long-term basis.

Comparative Example 2

Comparative Example 2 used as its working electrode the platinum electrode shown in FIG. 17 which was fabricated in a similar way to Comparative Example 1, and performed iterative measurement with glucose being its analyte similar to Embodiment 4. A result of the measurement revealed that the obtained variation range between the first and the 60,000th analyses was 4.2% as shown in FIG. 17.

Comparative Example 3

Comparative Example 3 used as its working electrode the platinum electrode shown in FIG. 17 which was formed in a similar way to Comparative Example 1, and performed iterative measurement with urea being its analyte similar to Embodiment 5. A result of the measurement revealed that the obtained variation range between the first and the 60,000th analyses was 3.7% as shown in FIG. 17.

Comparative Example 4

Comparative Example 4 used as its working electrode the platinum electrode shown in FIG. 17 which was formed in a similar way to Comparative Example 1, and performed iterative measurement with cholesterol being its analyte similar to Embodiment 6. A result of the measurement revealed that the obtained variation range between the first and the 60,000th analyses was 7.3% as shown in FIG. 17.

Comparative Example 5

Comparative Example 5 used as its working electrode the platinum electrode shown in FIG. 17 which was formed in a similar way to Comparative Example 1, and performed iterative measurement with uric acid being its analyte similar to Embodiment 7. A result of the measurement revealed that the obtained variation range between the first and the 60,000th analyses was 8.8% as shown in FIG. 17.

Comparative Example 6

Comparative Example 6 used as its working electrode the platinum electrode shown in FIG. 17 which was formed in a similar way to Comparative Example 1, and performed iterative measurement with creatinine being its analyte similar to Embodiment 8. A result of the measurement revealed that the obtained variation range between the first and the 60,000th analyses was 11.2% as shown in FIG. 17.

Comparative Example 7

Comparative Example 7 used as its working electrode the platinum electrode shown in FIG. 17 which was formed in a similar way to Comparative Example 1, and performed iterative measurement with creatinine being its analyte similar to Embodiment 9. A result of the measurement revealed that the obtained variation range between the first and the 60,000th analyses was 12.6% as shown in FIG. 17.

Comparative Example 8

Comparative Example 8 used as its working electrode the platinum electrode shown in FIG. 17 which was formed in a similar way to Comparative Example 1, and performed iterative measurement with fatty acid being its analyte similar to Embodiment 10. A result of the measurement revealed that the obtained variation range between the first and the 60,000th analysis was 7.2% as shown in FIG. 17.

Comparative Example 9

Comparative Example 9 used as its working electrode the platinum electrode shown in FIG. 17 which was formed in a similar way to Comparative Example 1, and performed iterative measurement with bilirubin being its analyte similar to Embodiment 11. A result of the measurement revealed that the obtained variation range between the first and the 60,000th analyses was 6.6% as shown in FIG. 17.

In the case of using the platinum electrodes of Comparative Examples 2 to 9, it is considered to be attributed to production of large step-like differences locally in the electrode plane by the etching rate difference within the electrode surface being large and a specific plane dissolving preferentially with repeated execution of analysis, that is, with the progress of surface etching. As a result, it is considered that the variation of the electrode surface state becomes large and it becomes impossible to stably perform liquid substitution of an analyte liquid and a cleaning fluid, thus causing the variation of the electrochemical response to become large when viewing on a long-term basis.

Next, Comparative Examples 10 to 18 shown in FIG. 24 will be explained.

Comparative Example 10

The electrode of Comparative Example 10 is a multilayer electrode of platinum and titanium. This electrode was pressed as of a platinum plate with a thickness of 1 mm and a titanium plate with a thickness of 0.5 mm at 30 MPa in vacuum. It was heated up to 800 degrees for 1 hour and hot rolled at 100 MPa so that the thickness of platinum part becomes 100 μm. After cooling, it was embedded into a fluorine-based resin similar to Embodiment 15 of the present invention, the platinum surface was subjected to mechanical polishing using water-proof abrasive paper, diamond paste, and alumina sequentially and continuously subjected to electrolytic polishing, thereby obtaining the working electrode.

Using this working electrode in the electrochemical analyzer of FIG. 1 similar to Embodiment 15, measurement was performed by a method for immunologically analyzing as the measurement solution TSH in blood serum and introducing as a cleaning fluid, for example, potassium hydroxide aqueous solution into the electrolysis cell at every completion of each measurement.

Figure 19:
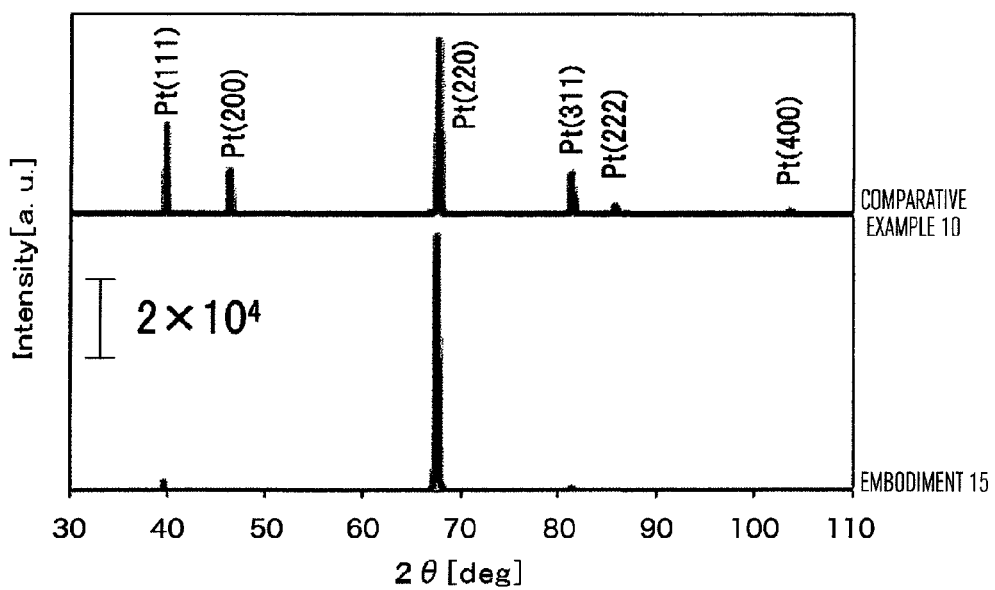
FIG. 19 is a diagram showing X-ray diffraction analysis results of electrodes of one embodiment of the present invention and one comparative example.

As a result, as shown in FIG. 21, a variation range in the case of using the electrode of Comparative Example 10 was about 10.3%. As the electrode of Comparative Example 10 was analyzed by X-ray diffraction, it was revealed to be preferentially oriented to (220) and (111) as shown in FIG. 19. The orientation ratio of the (220) direction exhibiting a maximal intensity was, however, found to be 54%.

Figure 23:
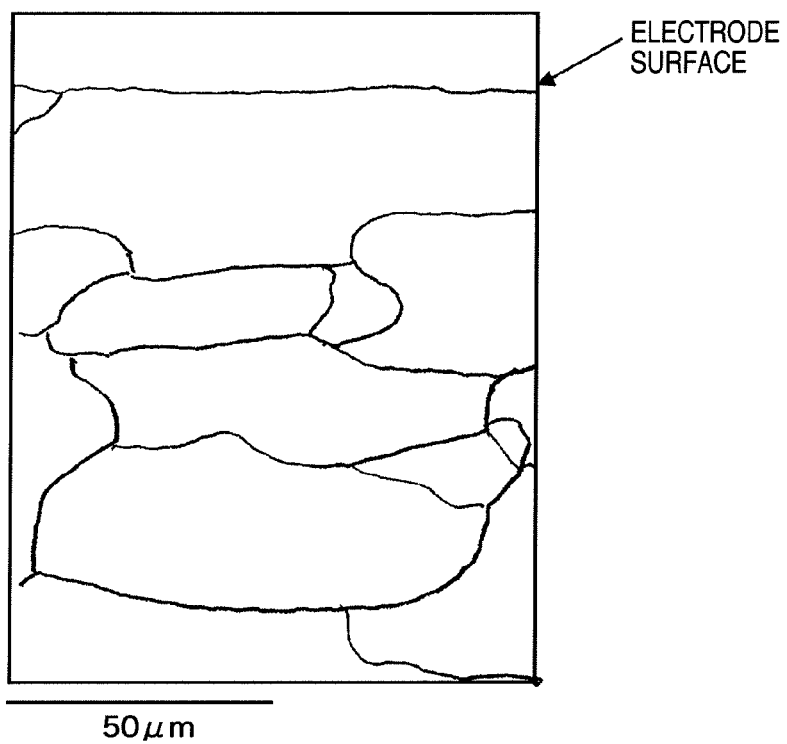
FIG. 23 is a diagram showing an analysis result of crystalline texture of a cross-section in the plate thickness direction of an electrode of one comparative example different from the present invention.

Additionally, upon observation of the crystal texture of a cross-section in the plate thickness direction of the platinum part by electron beam backscatter pattern analysis, it was found that the platinum has no layered form and grain sizes were extremely coarse as shown in FIG. 23.

In the case of using such the electrode, it is considered that the etching rate difference within the electrode surface becomes large with repeated execution of analysis, that is, with a progress of surface etching, causing the unevenness caused due to etching and the variation in the surface area to increase, resulting in the variation in the electrochemical response becoming large.

Comparative Example 11

Comparative Example 11 used as its working electrode the multilayer electrode of Comparative Example 10 with the crystal texture of the platinum part coarsened, and performed iterative measurement with glucose being the analyte similar to Embodiment 18. A result of the measurement revealed that as shown in FIG. 24, the obtained variation range between the first and the 60,000th analyses was 4.2%, which is greater than that of Embodiment 18.

Comparative Example 12

Comparative Example 12 used as its working electrode the multilayer electrode of Comparative Example 10 with the crystal texture of the platinum part coarsened, and performed iterative measurement with urea being the analyte similar to Embodiment 19. A result of the measurement revealed that as shown in FIG. 24, the obtained variation range between the first and the 60,000th analyses was 3.7%, which is greater than that of Embodiment 19.

Comparative Example 13

Comparative Example 13 used as its working electrode the multilayer electrode of Comparative Example 10 with the crystal texture of the platinum part coarsened, and performed iterative measurement with cholesterol being the analyte similar to Embodiment 20. A result of the measurement revealed that as shown in FIG. 24, the obtained variation range between the first and the 60,000th analyses was 7.3%, which is greater than that of Embodiment 20.

Comparative Example 14

Comparative Example 14 used as its working electrode the multilayer electrode of Comparative Example 10 with the crystal texture of the platinum part coarsened, and performed iterative measurement with uric acid being the analyte similar to Embodiment 21. A result of the measurement revealed that as shown in FIG. 24, the obtained variation range between the first and the 60,000th analyses was 8.8%, which is greater than that of Embodiment 21.

Comparative Example 15

Comparative Example 15 used as its working electrode the multilayer electrode of Comparative Example 10 with the crystal texture of the platinum part coarsened, and performed iterative measurement with creatinine being the analyte similar to Embodiment 22. A result of the measurement revealed that as shown in FIG. 24, the obtained variation range between the first and the 60,000th analyses was 11.2%, which is greater than that of Embodiment 22.

Comparative Example 16

Comparative Example 16 used as its working electrode the multilayer electrode of Comparative Example 10 with the crystal texture of the platinum part coarsened, and performed iterative measurement with creatinine being the analyte similar to Embodiment 23. A result of the measurement revealed that as shown in FIG. 24, the obtained variation range between the first and the 60,000th analyses was 12.6%, which is greater than that of Embodiment 23.

Comparative Example 17

Comparative Example 17 used as its working electrode the multilayer electrode of Comparative Example 10 with the crystal texture of the platinum part coarsened, and performed iterative measurement with fatty acid being the analyte similar to Embodiment 24. A result of the measurement revealed that as shown in FIG. 24, the obtained variation range between the first and the 60,000th analyses was 7.2%, which is greater than that of Embodiment 24.

Comparative Example 18

Comparative Example 18 used as its working electrode the multilayer electrode of Comparative Example 10 with the crystal texture of the platinum part coarsened, and performed iterative measurement with bilirubin being the analyte similar to Embodiment 25. A result of the measurement revealed that as shown in FIG. 24, the obtained variation range between the first and the 60,000th analyses was 6.6%, which is greater than that of Embodiment 25.

It is considered that in the case of using such the multilayer electrodes of Comparative Examples 11 to 18, the etching rate difference within the electrode surface becomes large with repeated execution of analysis, that is, with a progress of surface etching, causing the unevenness caused due to etching and the variation in the surface area to increase, resulting in the variation in the electrochemical response becoming large.

It should be noted that, although the above-stated embodiments of the present invention are examples where the present invention was applied to the working electrode of an electrochemical analysis apparatus, this invention may be applicable not only to the working electrode but also to the counter electrode. Also applying the present invention to the counter electrode makes it possible to further achieve a high accuracy of analysis data.

It should be further understood by those skilled in the art that although the foregoing description has been made on embodiments of the invention, the invention is not limited thereto and various changes and modifications may be made without departing from the spirit of the invention and the scope of the appended claims.

REFERENCE SIGNS LIST

1 Electrolysis Cell
2, 34, 74, 104, 134, 194 Working Electrode
3, 35, 75, 105, 135, 195 Counter Electrode
4 Reference Electrode
5 Potential-Applying Means
6 Measuring Means
7, 39, 40, 79, 80, 109, 110, 139, 140, 199, 200, 302 Lead Wire
8 Measurement Solution Vessel
9 Buffer Fluid Vessel
10 Cleaning Liquid Vessel
11 Solution-Dispensing Mechanism
12 Solution Injection Mechanism
13 Solution Inlet Pipe
14 Solution Outlet Pipe
15 Solution Exhaust (Suction) Mechanism
16 Waste Container
20, 60, 90, 120, 180 Flow Cell
21, 22 Hole
30, 32, 70, 72, 100, 102, 130, 132, 190 Insulative Substrate
192 Insulative Chassis
31, 71, 101, 131 Sealing Member
33, 73, 103, 133, 193 Screw Hole
36, 76, 106, 136 Opening
37, 38, 77, 78, 107, 108, 137, 138, 197, 198 Pipe
50 Working Electrode Manufacturing Apparatus
50a Electroding Unit
50b Resin Embedding Unit
50c Mechanical Polishing Unit
50d Electrolytic Polishing Unit
52 Working Electrode Manufacturing Apparatus
52a Platinum Plate Machining Unit
52b Platinum Plate Cold Rolling Unit
52c Surface Oxide Film Removing Unit
52d Multilayer Electrode Forming Unit
52e Cutting Unit
52f Electroding Unit
52g Resin Embedding Unit
52h Mechanical Polishing Unit
52i Potential Scanning Unit
141 Electrically Connecting Bolt
142 Electrically Connecting Plate
143 Thread
191 O-Ring
300 Insulative Resin
301 Composite Material
303 Adhesive Agent
304 Shaft

The invention claimed is:

1. An electrode for electrochemical measurement to be used in an electrochemical analysis apparatus which measures electrochemical response of a chemical component contained in a liquid sample, the electrode made by connecting a lead wire to a composite material consisting of a base material and an oxide of a metal, the oxide of a metal selected from a group consisting of zirconium, tantalum, and niobium, and is dispersed in the base material, the base material being made of platinum or a platinum alloy, wherein a content ratio of the oxide of a metal is 0.005 to 1 weight percent (wt %).

2. The electrode for electrochemical measurement according to claim 1, wherein an orientation ratio of one of a plurality of crystal directions obtained is 80% or greater when letting the orientation ratio (%) of a crystal direction obtained by X-ray diffraction measurement of a surface of the electrode be $I(hkl)/\Sigma I(hkl) \times 100$ (where $I(hkl)$ is a diffraction intensity integration value of each plane, and $\Sigma I(hkl)$ is a total sum of diffraction intensity integration values of (hkl)).

3. The electrode for electrochemical measurement according to claim 1, wherein a material of an electrode is embedded in an insulative resin except for a part of a surface of the electrode.

4. An electrolysis cell for measuring electrochemical response of a chemical component contained in a liquid sample, the electrolysis cell having a working electrode, a counter electrode, and a reference electrode disposed therein, the working electrode being the electrode according to claim 1.

5. The electrolysis cell according to claim 4, wherein the electrolysis cell is a flow cell to which an injection port for injecting into the cell and an exhaust port for exhausting to outside a liquid sample are disposed.

6. An electrochemical analysis apparatus comprising:
an electrolysis cell having a working electrode, a counter electrode, and a reference electrode disposed therein;
a solution injection device which injects into the electrolysis cell a solution under measurement, a buffer solution, and a cleaning solution;
a potential application device which applies potentials to the working electrode, the counter electrode, and the reference electrode; and
a measuring device which is connected to the working electrode, the counter electrode, and the reference electrode and measures electrochemical characteristics of the solution under measurement,
the working electrode being an electrode according to claim 1.

\* \* \* \* \*